US011549093B2

(12) United States Patent
Tatsuta et al.

(10) Patent No.: US 11,549,093 B2
(45) Date of Patent: Jan. 10, 2023

(54) MEASUREMENT APPARATUS

(71) Applicant: SONY CORPORATION, Tokyo (JP)

(72) Inventors: Hirokazu Tatsuta, Kanagawa (JP);
Takeshi Kunihiro, Kanagawa (JP);
Kazuhiro Nakagawa, Saiatama (JP)

(73) Assignee: SONY CORPORATION, Tokyo (JP)

( * ) Notice: Subject to any disclaimer, the term of this patent is extended or adjusted under 35 U.S.C. 154(b) by 241 days.

(21) Appl. No.: 16/621,793

(22) PCT Filed: May 18, 2018

(86) PCT No.: PCT/JP2018/019237
§ 371 (c)(1),
(2) Date: Dec. 12, 2019

(87) PCT Pub. No.: WO2018/235477
PCT Pub. Date: Dec. 27, 2018

(65) Prior Publication Data
US 2020/0172848 A1 Jun. 4, 2020

(30) Foreign Application Priority Data

Jun. 22, 2017 (JP) .............................. JP2017-122091

(51) Int. Cl.
*C12M 3/00* (2006.01)
*C12M 1/00* (2006.01)
(Continued)

(52) U.S. Cl.
CPC ............ *C12M 41/06* (2013.01); *C12M 31/00* (2013.01); *C12M 31/08* (2013.01); *C12M 41/36* (2013.01);
(Continued)

(58) Field of Classification Search
CPC .................. C12M 41/06; C12M 31/00; G01N 2015/0065; G01N 2015/1454
See application file for complete search history.

(56) References Cited

U.S. PATENT DOCUMENTS

2007/0263210 A1* 11/2007 Taguchi ................ B01L 3/0275
356/318
2010/0188665 A1*  7/2010 Dotson .................. G01N 21/45
356/517
(Continued)

FOREIGN PATENT DOCUMENTS

CN        104136907 A     11/2014
EP          2602608 A1     6/2013
(Continued)

OTHER PUBLICATIONS

International Search Report and Written Opinion of PCT Application No. PCT/JP2018/019237, dated Aug. 7, 2018, 12 pages of ISRWO.

*Primary Examiner* — Nathan A Bowers
(74) *Attorney, Agent, or Firm* — Chip Law Group

(57) ABSTRACT

A measurement apparatus according to an embodiment of the present technology includes a light source, a filling portion, and a detector. The light source emits illumination light. The filling portion includes a first surface portion and a second surface portion which are provided on an optical path of the illumination light and are opposite to each other, the filling portion enabling a cavity between the first and second surface portions to be filled with liquid including a cell. The detector detects an interference fringe of the illumination light passing through the cavity, the interference fringe being caused by the liquid including the cell.

18 Claims, 17 Drawing Sheets

(51) Int. Cl.
    *C12M 1/34*     (2006.01)
    *G01N 15/14*    (2006.01)
    *G01N 15/00*    (2006.01)

(52) U.S. Cl.
    CPC . *G01N 15/1436* (2013.01); *G01N 2015/0065* (2013.01); *G01N 2015/1452* (2013.01); *G01N 2015/1486* (2013.01)

(56) References Cited

U.S. PATENT DOCUMENTS

| | | | |
|---|---|---|---|
| 2010/0284016 A1* | 11/2010 | Teitell | G01J 3/453 356/451 |
| 2013/0288286 A1* | 10/2013 | Sugiyama | G01N 21/4788 435/29 |
| 2014/0376816 A1 | 12/2014 | Lagae et al. | |
| 2016/0160174 A1 | 6/2016 | Allier | |
| 2016/0349165 A1 | 12/2016 | Kawano et al. | |
| 2016/0349170 A1* | 12/2016 | Nakatsuji | G01N 15/1434 |
| 2018/0024127 A1* | 1/2018 | Ng | G01N 33/54373 422/69 |
| 2018/0025475 A1* | 1/2018 | Kato | G06T 5/50 348/241 |
| 2018/0113290 A1* | 4/2018 | Chan | G02B 21/086 |

FOREIGN PATENT DOCUMENTS

| | | |
|---|---|---|
| EP | 3101410 A1 | 12/2016 |
| FR | 3009084 A | 1/2015 |
| JP | 2007-006852 A | 1/2007 |
| JP | 2009-218478 A | 9/2009 |
| JP | 2012-013686 A | 1/2012 |
| JP | 2014-115077 A | 6/2014 |
| JP | 2015-500475 A | 1/2015 |
| JP | 2016-034235 A | 3/2016 |
| JP | 2016-529493 A | 9/2016 |
| WO | 2012/132930 A1 | 10/2012 |
| WO | 2013/083815 A1 | 6/2013 |
| WO | 2015/011096 A1 | 1/2015 |
| WO | 2015/115471 A1 | 8/2015 |

\* cited by examiner a (z=0)

a (L < z < L + t)

MEASUREMENT APPARATUS

CROSS REFERENCE TO RELATED APPLICATIONS

This application is a U.S. National Phase of International Patent Application No. PCT/JP2018/019237 filed on May 18, 2018, which claims priority benefit of Japanese Patent Application No. JP 2017-122091 filed in the Japan Patent Office on Jun. 22, 2017. Each of the above-referenced applications is hereby incorporated herein by reference in its entirety.

TECHNICAL FIELD

The present technology relates to a measurement apparatus to be used for sensing a cell.

BACKGROUND ART

Conventionally, there is known a technology of sensing a cell. For example, Patent Literature 1 describes a microscope that observes a cell cultured in a culture vessel. In Patent Literature 1, a culture vessel such as a dish is set on a stage in a stationary state. The stage is moved in upper and lower directions to perform focus control on a cell junction surface, a culture medium surface, or the like on the basis of information regarding the type of culture vessel, the amount of culture medium, and the like that a user specifies. The microscope takes images of respective surfaces. The taken images of the respective surfaces are compared and investigated. In this manner, information regarding a growing condition of a cell which is a sample can be automatically acquired (paragraphs [0011], [0013], [0028], and [0029] of specification, FIG. 1, FIG. 4, and the like of Patent Literature 1).

CITATION LIST

Patent Literature

Patent Literature 1: Japanese Patent Application Laid-open No. 2007-6852

DISCLOSURE OF INVENTION

Technical Problem

In a cell-producing process such as cell culture, it is important to sense and manage states of cells, a culture medium, and the like. Therefore, it is desirable to provide a technology by which states of cells and the like can be easily sensed in real time.

In view of the above-mentioned circumstances, it is an object of the present technology to provide a measurement apparatus by which states of cells and the like can be easily sensed in real time.

Solution to Problem

In order to accomplish the above-mentioned object, a measurement apparatus according to an embodiment of the present technology includes a light source, a filling portion, and a detector.

The light source emits illumination light.

The filling portion includes a first surface portion and a second surface portion which are provided on an optical path of the illumination light and are opposite to each other, the filling portion enabling a cavity between the first and second surface portions to be filled with liquid including a cell.

The detector detects an interference fringe of the illumination light passing through the cavity, the interference fringe being caused by the liquid including the cell.

In this measurement apparatus, the cavity sandwiched by the first and second surface portions opposite to each other is provided on the optical path of the illumination light emitted from the light source. This cavity is filled with the liquid including the cell. Then, the interference fringe of the illumination light which is caused by the liquid including the cell which fills the cavity is detected. With this configuration, states of the cell and the like can be easily sensed in real time on the basis of the interference fringe.

The filling portion may have a width from the first surface portion to the second surface portion of the cavity which is set in a manner that depends on a parameters regarding the cell.

With this configuration, the width of the cavity filled with the liquid including the cell can be properly set in a manner that depends on characteristics and the like of the cell. States of the cell and the like can be sensed with high precision.

The parameter regarding the cell may include at least one of a size of the cell or a concentration of the cell in the liquid.

For example, the width of the cavity can be set on the basis of the size of the cell or the concentration of the cell included in the liquid. With this configuration, states of the cell and the like can be sensed with high precision.

The detector may have a detection surface approximately perpendicular to an optical path of the illumination light. In this case, the filling portion may have a detection space depending on the detection surface.

The illumination light passes through the detection space filled with the liquid including the cell and enters the detection surface, for example. With this configuration, states of the cell and the like can be easily sensed.

The width of the cavity may be set such that total sum of cross-sectional areas of the cells included in the detection space is smaller than the detection surface.

With this configuration, the illumination light diffracted by the respective cells in the liquid can be precisely detected, for example. As a result, states of the cells and the like can be sensed with sufficiently high precision.

The width of the cavity may be set such that an area of a region in which cells each being the cell are packed in a case where the cells included in the detection space are two-dimensionally close-packed is smaller than the detection surface.

With this configuration, the illumination light diffracted by the respective cells in the liquid can be precisely detected, for example. As a result, states of the cells and the like can be sensed with sufficiently high precision.

The width of the cavity may be smaller than 11.8 mm.

With this configuration, states of the cells and the like with a desired concentration can be sensed.

The illumination light may be approximately coherent light or partially-coherent light.

With this configuration, the coherence of the illumination light is enhanced, for example, and an interference fringe caused by the cell can be detected with high precision. As a result, states of the cell and the like can be sensed with high precision.

The first surface portion may include a first optical window that the illumination light emitted from the light source enters. In this case, the second surface portion may include a second optical window which is arranged approximately parallel to the first optical window and emits the illumination light passing through the filling portion.

By using the first and second optical windows, the interference fringe of the illumination light can be precisely detected, for example. With this configuration, the precision of sensing can be enhanced.

The first optical window may be an optical filter that permits some wavelength components of the illumination light to pass therethrough.

For example, the coherence of the illumination light can be enhanced by narrowing the wavelength range of the illumination light through the optical filter. With this configuration, the precision of sensing can be enhanced.

The measurement apparatus may further include a collimator which is arranged between the light source and the filling portion and collimates the illumination light.

With this configuration, the illumination light can be radiated to the liquid including the cell as an approximately parallel luminous flux. States of the cell and the like can be sensed with high precision.

The detector may generate image data in which an interference fringe of the illumination light is recorded.

With this configuration, states of cells and the like can be easily analyzed on the basis of the image data.

The light source may be capable of switching and emitting light beams having wavelengths different from each other as the illumination light. In this case, the detector may generate a plurality of pieces of image data respectively corresponding to the light beams having wavelengths different from each other.

With this configuration, for example, the color and the like of the liquid including the cell can be sensed.

The measurement apparatus may further include a color-information calculation unit that calculates color information of the liquid including the cell on the basis of the plurality of pieces of image data.

The state of the liquid including the cell and the like can be analyzed, for example, on the basis of the color information.

The cell may include an immune cell.

With this configuration, a state of the immune cell can be easily sensed in real time.

The liquid including the cell may include a liquid culture medium to which a pH indicator is added.

For example, the pH of the liquid culture medium and the like can be calculated on the basis of the color information of the liquid culture medium. The state and the like of the culture environment can be thus easily sensed.

The above-mentioned measurement apparatus may be put in the liquid including the cell.

For example, the measurement apparatus is enabled to operate in a state in which the measurement apparatus is immerged in the liquid culture medium or the like. As a result, states of the cell and the like can be easily sensed in real time.

Advantageous Effects of Invention

As described above, in accordance with the present technology, states of cells and the like can be easily sensed in real time. It should be noted that the effects described here are not necessarily limitative and any effect described in the present disclosure may be provided.

MODE(S) FOR CARRYING OUT THE INVENTION

Hereinafter, embodiments according to the present technology will be described with reference to the drawings.

[Configuration of Measurement System]

Figure 1:
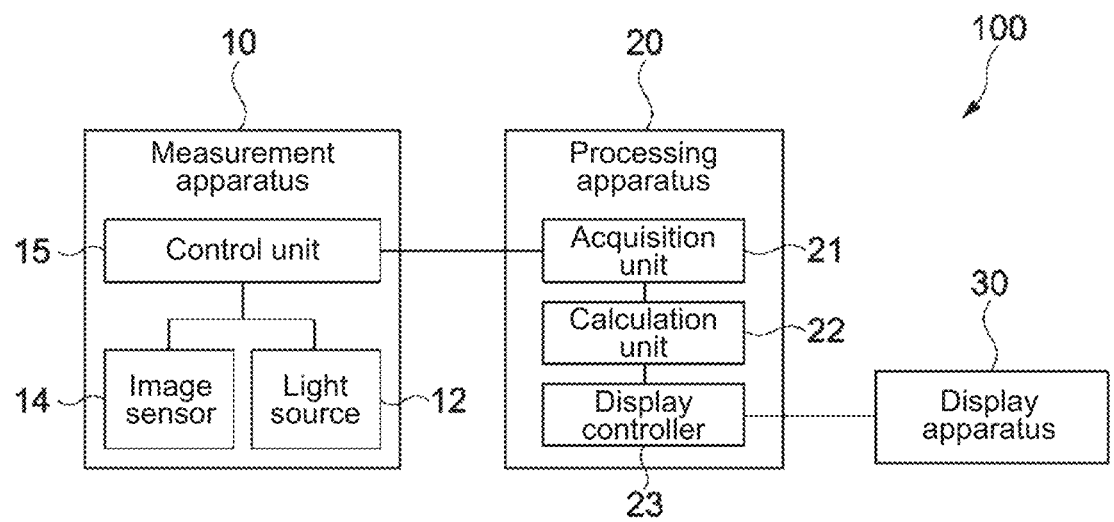
FIG. 1 A block diagram showing a configuration example of a measurement system according to the present technology.

FIG. 1 is a block diagram showing a configuration example of a measurement system according to the present technology. A measurement system 100 includes a measurement apparatus 10, a processing apparatus 20, and a display apparatus 30.

Figure 2:
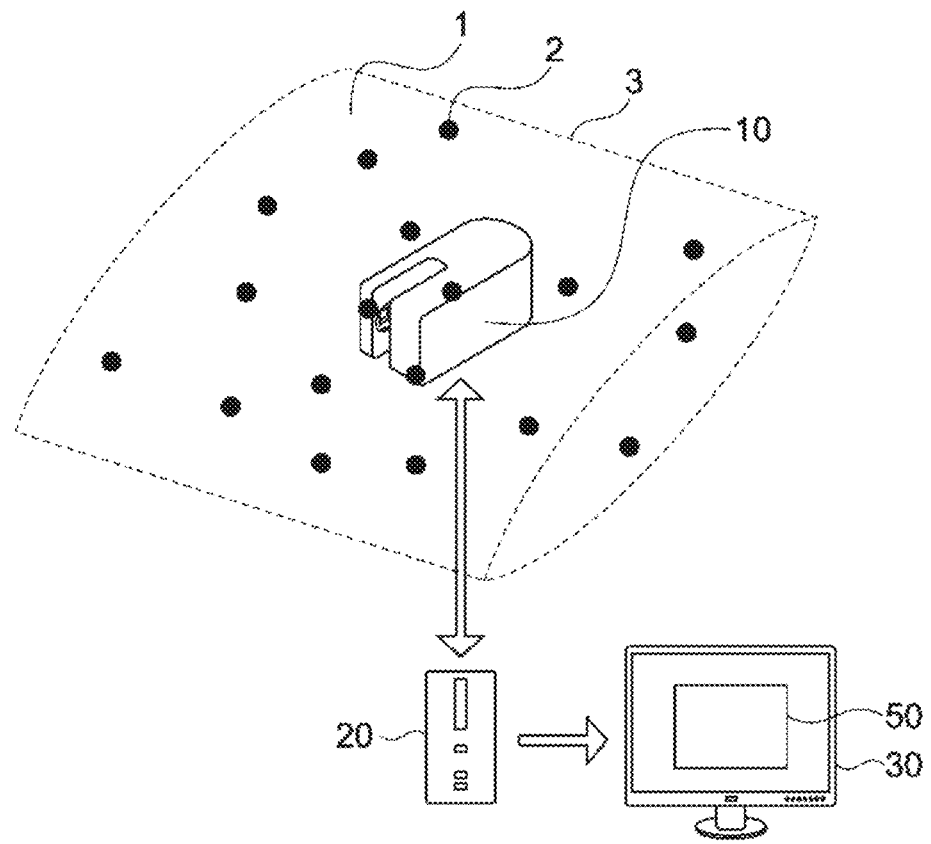
FIG. 2 A schematic view for describing an overview of the measurement system.

FIG. 2 is a schematic view for describing an overview of the measurement system 100. In this embodiment, the measurement system 100 senses cells 2 floating in culture solution 1. It should be noted that in FIG. 2, the cells 2 floating in the culture solution 1 are schematically shown as the dots and a pack 3 filled with the culture solution 1 including the cells 2 is schematically shown as the dashed lines.

In this embodiment, the cells 2 are immune cells. As a matter of course, the cells 2 are not limited thereto. For example, the present technology is applicable to arbitrary cells floating in the liquid. In the present specification, the "cell" (singular) at least conceptually includes a single cell and a group of a plurality of cells.

The culture solution 1 is a liquid culture medium to which a pH indicator is added. The culture solution 1 is configured to include a nutrient and the like required for growth and increase of immune cells, for example. For example, phenol red and the like are used as the pH indicator. A specific configuration of the culture solution 1, the type of pH indicator, and the like are not limited. In this embodiment, the culture solution 1 corresponds to liquid including a cell.

The pack 3 is a culture vessel for culturing the cells 2. Using the culture solution 1 as a culture medium, suspension culture of the cells 2 (immune cells) floating in the culture solution 1 is performed inside the pack 3. It should be noted that the present technology is not limited to the case where the pack 3 is used as the culture vessel. For example, the present technology is also applicable to a case where another culture vessel such as a culture tank is used.

As shown in FIG. 2, in the measurement system 100, the measurement apparatus 10 is put inside the pack 3. That is, the measurement apparatus 10 is put in the culture solution 1 including the cells 2. For example, the measurement apparatus 10 measures states and the like of the cells 2 and the culture solution 1. The measurement result is output to the processing apparatus 20 put outside the pack 3. The processing apparatus 20 performs processing related to the measurement result. The processing result is displayed on the display apparatus 30. Accordingly, the states and the like of the cultured cells can be monitored.

Specifically, a light source 12, an image sensor 14, and a control unit 15 of the measurement apparatus 10 shown in FIG. 1 cooperate with one another. With this cooperation, interference fringes of illumination light are detected. The interference fringes of illumination light are caused by the culture solution 1 including the cells 2. Then, image data in which the interference fringes are recorded is generated.

Moreover, an acquisition unit 21, a calculation unit 22, and a display controller 23 cooperate with one another in the processing apparatus 20. With this cooperation, cell information regarding the cells 2 is calculated on the basis of the image data. Display of a monitoring image 50 indicating a temporal change in the cell information is controlled. Then, the monitoring image 50 is displayed on the display apparatus 30. Hereinafter, the respective blocks of the measurement system 100 will be described.

Figure 3:
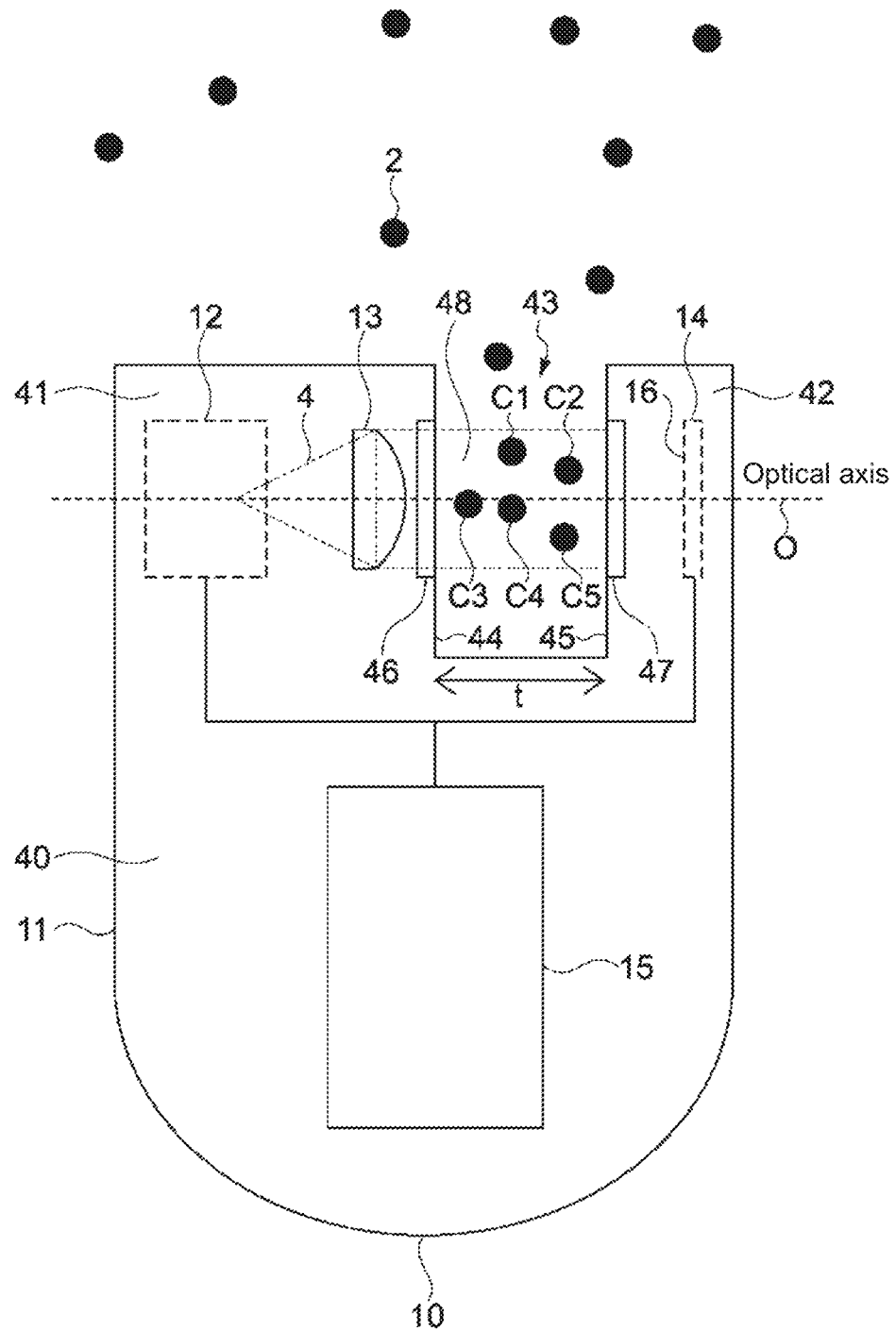
FIG. 3 A schematic view showing a configuration example of a measurement apparatus.
Figure 4:
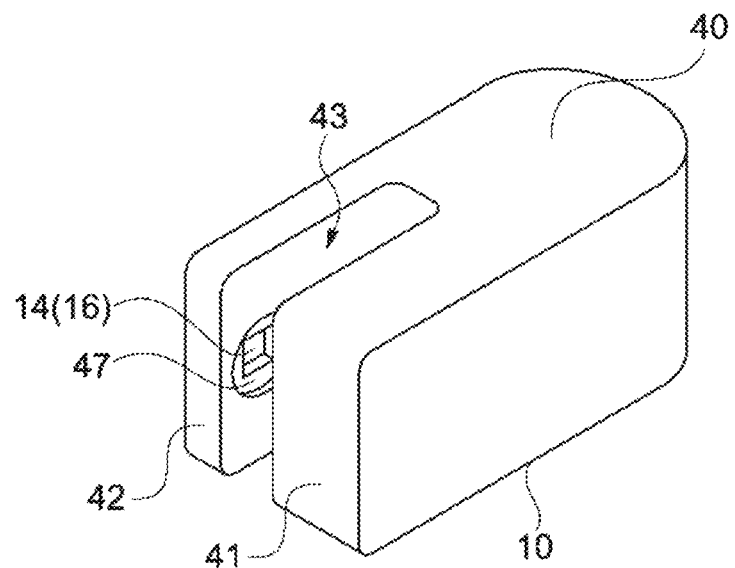
FIG. 4 A perspective view showing an example of an outer appearance of the measurement apparatus.

FIG. 3 is a schematic view showing a configuration example of the measurement apparatus 10. FIG. 4 is a perspective view showing an example of an outer appearance of the measurement apparatus 10. The measurement apparatus 10 includes a casing 11, a light source 12, a collimator lens 13, an image sensor 14, and the control unit 15.

The casing 11 includes a base portion 40, a first protrusion portion 41, and a second protrusion portion 42. The first protrusion portion 41 and the second protrusion portion 42 protrude from the base portion 40. The first and second protrusion portions 41 and 42 protrude from the base portion 40 in the same direction. The first and second protrusion portions 41 and 42 face each other, spaced apart from each other with a predetermined distance t therebetween. A cavity 43 is formed between the first and second protrusion portions 41 and 42. The cavity 43 has a width (referred to as a width t with the same reference sign) equivalent to the predetermined distance t.

A first surface 44 and a second surface 45 are each formed in the first and second protrusion portions 41 and 42. The first surface 44 and the second surface 45 face each other with the cavity 43 formed therebetween. In this embodiment, the first and second protrusion portions 41 and 42 form a filling portion. The cavity 43 between the first and second surfaces 44 and 45 is filled with the culture solution 1. It should be noted that the first surface 44 and the second surface 45 respectively correspond to a first surface portion and a second surface portion.

The first surface 44 includes a first optical window 46. Illumination light 4 is emitted from the light source 12 to be described later. The emitted illumination light 4 enters the first optical window 46. The first optical window 46 is arranged to be approximately perpendicular to an optical-path direction of the illumination light 4, for example.

In this embodiment, the first optical window 46 functions as an optical filter that permits some wavelength components of the illumination light 4 to pass therethrough. A band pass filter including a dielectric multilayer film and the like, for example, is used as the first optical window 46. In this case, the passband of the filter is set as appropriate to narrow the wavelength range of the illumination light 4. Accordingly, the wavelength range of the illumination light 4 can be sharpened and the coherence of the illumination light 4 can be enhanced.

The second surface 45 includes a second optical window 47. The second optical window 47 is arranged to be approximately parallel to the first optical window 46. The illumination light 4 that passes through the cavity 43 is emitted from the second optical window 47. A transparent plate made of glass, crystal, or the like, for example, is used as the second optical window 47 as appropriate.

The casing 11 functions as an outer casing of the measurement apparatus 10. The casing 11 is configured to prevent liquid and the like from entering the casing 11. An outer surface of the casing 11 is coated with a material harmless to the cells 2 and the like. Moreover, the casing 11 has a streamlined part. In this embodiment, a surface of the base portion 40, which is opposite to a portion connected to the first and second protrusion portions 41 and 42, is constituted by a curved surface.

Such a configuration of the casing 11 can sufficiently reduce the influence of the measurement apparatus 10 on the cultured cells 2, the culture environment, and the like. Accordingly, states of cells and the like can be properly sensed without prohibiting flow of liquid such as the culture solution 1, for example. It should be noted that a specific configuration and the like of the casing 11 are not limited. The casing 11 may be configured as appropriate in a manner that depends on an environment where the casing 11 is used and the like.

The light source 12 is arranged inside the first protrusion portion 41, directed to the second protrusion portion 42. The light source 12 emits the illumination light 4 along an optical axis O toward the second protrusion portion 42. It should be noted that in FIG. 3, the optical axis O of the light source 12 is shown as the dashed lines. Hereinafter, a direction parallel to the optical axis O is referred to as a Z axis direction. In this embodiment, the direction parallel to the optical axis O, i.e., the Z axis direction corresponds to the optical-path direction of the illumination light.

In this embodiment, the illumination light 4 emitted from the light source 12 is partially-coherent light. A light emitting diode (LED) light source or the like capable of emitting single-color light having a predetermined wavelength spectrum, for example, is used as the light source 12. A specific configuration of the light source 12 is not limited. An arbitrary light source capable of emitting partially-coherent light, for example, may be used.

Moreover, the light source 12 is capable of switching and emitting light beams having wavelengths different from each other as the illumination light 4. The light source 12 is configured to include a plurality of LED light sources or the like each capable of emitting light beams having wavelengths different from each other, for example. Accordingly, the wavelength of a light beam to be emitted as the illumination light 4 can be switched as appropriate. Additionally or alternatively, an arbitrary configuration capable of switching and emitting light beams having wavelengths different from each other may be used.

In this embodiment, the light source 12 is capable of switching and emitting each of three types of light, which correspond to the wavelengths of red light R, green light G, and blue light B. It should be noted that the center wavelength, the bandwidth, and the like of the respective color light beams are not limited. In this embodiment, the light source 12 corresponds to a light source that emits illumination light.

The collimator lens 13 is arranged between the light source 12 and the cavity 43, inside the first protrusion portion 41. The collimator lens 13 is arranged on the optical axis O. The collimator lens 13 collimates the illumination light 4 emitted from the light source 12. The illumination light 4 passing through the collimator lens 13 is emitted as an approximately parallel luminous flux. In this embodiment, the collimator lens 13 corresponds to a collimator.

As shown in FIG. 3, the illumination light 4, which is the approximately parallel luminous flux, passes through the first surface 44 (the first optical window 46), the cavity 43, and the second surface 45 (the second optical window 47) in the stated order. The first surface 44 (the first optical window 46), the cavity 43, and the second surface 45 (the second optical window 47) are provided on the optical path of the illumination light 4. Then, the illumination light 4 enters the second protrusion portion 42.

The image sensor 14 has a detection surface 16 approximately perpendicular to the optical axis O of the illumination light 4. The image sensor 14 is arranged inside the second protrusion portion 42 such that the detection surface 16 faces the second optical window 47. Therefore, the illumination light 4 passing through the culture solution 1 including the cells 2, which fills the cavity 43, enters the detection surface 16.

The image sensor 14 receives the illumination light 4 entering the detection surface 16. The image sensor 14 detects interference fringes of the illumination light 4 passing through the cavity 43, which are caused by the culture solution 1 including the cells 2. Moreover, the image sensor 14 generates image data in which the interference fringes of the illumination light 4 are recorded.

The image sensor 14 functions as a monochrome image sensor having a light-receiving surface. At a monochrome image sensor, the intensity (luminance) of the illumination light 4 at each position on the light-receiving surface, for example, is detected. It should be noted that in the example shown in FIG. 3, the light-receiving surface of the image sensor 14 corresponds to the detection surface 16. A charge coupled device (CCD) sensor, a complementary metal-oxide semiconductor (CMOS) sensor, or the like is used as the image sensor 14, for example. As a matter of course, another type of sensor or the like may be used.

The control unit 15 controls operations of the respective blocks of the measurement apparatus 10. For example, the control unit 15 controls timings and the like of switching of the wavelength of the illumination light 4 emitted from the light source 12 and operations of the image sensor 14.

Moreover, the control unit 15 has a communication function for communicating with external devices of the measurement apparatus 10. The control unit 15 is capable of sending and receiving image data and control signals and the like for controlling the respective blocks of the measurement apparatus to/from the processing apparatus 20. A specific configuration and the like of the control unit 15 are not limited. For example, a device such as a field programmable gate array (FPGA) and an application specific integrated circuit (ASIC) may be used.

Figure 5:
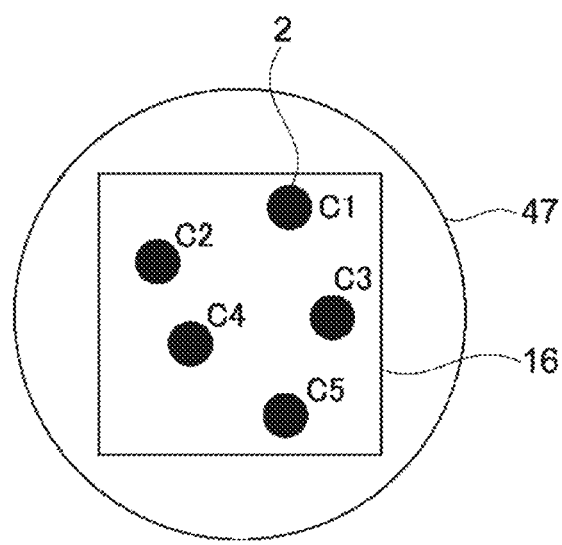
FIG. 5 A schematic view showing a positional relationship between a detection surface and cells as viewed in an optical-path direction of illumination light.

FIG. 5 is a schematic view showing a positional relationship between the detection surface 16 and the cells 2 as viewed in the optical-path direction of the illumination light 4. FIG. 5 schematically shows the second optical window 47 having a circular shape and the detection surface 16 having a rectangular shape. The detection surface 16 is arranged inside the second optical window 47. It should be noted that the cells C1 to C5 respectively the cells C1 to C5 floating in the cavity 43 of the measurement apparatus 10 described above with reference to FIG. 3.

As described above, the illumination light 4 enters the cavity 43 through the first optical window 46. For example, a part of the illumination light 4 entering the cavity 43 is diffracted by the cells 2 included in the culture solution 1 filling the cavity 43. Moreover, another part of the illumination light 4 travels straight in the culture solution 1 without being diffracted by the cells 2. As a result, light interference of the illumination light 4 diffracted by the cells 2 and the illumination light 4 travelling straight in the culture solution 1 occurs. The image sensor 14 detects interference fringes produced on the detection surface 16 (light-receiving surface) due to this light interference.

In this manner, the cells 2 floating on the optical path of the illumination light 4 entering the detection surface 16 produce the interference fringes of the illumination light 4. For example, in FIGS. 3 and 5, the interference fringes detected by the image sensor 14 are the interference fringes produced due to diffraction of the illumination light 4 due to the cells C1 to C5. Hereinafter, the inner space of the cavity 43 through which the illumination light 4 entering the detection surface 16 passes will be referred to as a detection space 48.

The detection space 48 has a bottom surface having the same shape as the detection surface 16, for example. The detection space 48 is a columnar space having the width t of the cavity as the height. The illumination light 4 passing through the detection space 48 travels in the culture solution 1 by a distance approximately equal to the width t of the cavity. Therefore, for example, as the width t of the cavity becomes longer, the number of cells 2 floating on the optical path of the illumination light 4 increases. Further, the frequency at which the illumination light 4 is diffracted by the cells 2 increases.

In this embodiment, the width t from the first surface 44 to the second surface 45 of the cavity 43 is set in a manner that depends on parameters regarding the cells 2. That is, it can also be said that the size of the detection space 48 in the Z axis direction set in a manner that depends on the parameters regarding the cells 2. Sizes of the cells 2 and a concentration of the cells 2 in the culture solution 1 are used as the parameters regarding the cells.

For example, when the second optical window 47 is viewed in the optical-path direction of the illumination light 4 as shown in FIG. 5, cross-sections (dot regions) of the cells 2 can be considered as a region in which diffraction of the illumination light 4 occurs. Therefore, as the sizes of the cells 2 (dot diameters) are larger, the region in which diffraction occurs is larger. Moreover, also as the concentration of the cells 2 is higher, the region in which diffraction occurs is larger because the number of cells 2 increases.

In this embodiment, the width t of the cavity 43 is set such that the total sum of the cross-sectional areas of the cells 2 included in the detection space 48 is smaller than the detection surface. The total sum of the cross-sectional areas of the cells 2 included in the detection space 48 $\Sigma$ is expressed in accordance with the expression below using the volume of the detection space 48 (an area S of the detection surface 16×the width t of the cavity 43), the sizes of the cells 2 (cross-sectional areas A of the cells 2), and a concentration N of the cells 2 in the culture solution 1, for example.

$$\Sigma = S \times t \times N \times A$$

When a sum $\Sigma$ of the cross-sectional areas is smaller than the area S of the detection surface 16 ($\Sigma < S$), the width t of the cavity 43 is expressed as $t < 1/(N \times A)$ using the cross-sectional areas A and the concentration N of the cells. In this manner, the width t of the cavity 43 is set to be a smaller value as the concentration N and the cross-sectional areas A are larger. On the other hand, when the concentration N and the cross-sectional areas A are smaller, the width t of the cavity 43 can be set to be thicker.

The sum $\Sigma$ of the cross-sectional areas corresponds to the area of the region in which diffraction occurs on the optical path of the illumination light 4. Therefore, the region in which diffraction occurs can be made smaller than the detection surface 16 by setting the width t of the cavity 43 as appropriate such that the sum $\Sigma$ of the cross-sectional areas is smaller than the area S of the detection surface 16.

Accordingly, for example, lowering of the coherence of the illumination light 4 due to diffraction of the illumination light 4 which is caused by the cells 2 several times when the illumination light 4 passes through the detection space 48 can be sufficiently suppressed. As a result, for example, blurring of interference fringes produced on the detection surface 16 can be avoided. The cells 2 can be thus sensed with high precision.

For example, Car-T cells used for immunotherapy of lymphocytic leukemia and the like are dosed to a patient with a concentration of about 30 cell/mm$^3$. For example, it is assumed that the mean diameter of Car-T cells is 6 μm and liquid including Car-T cells with a concentration (3000 cells/mm$^3$) hundred times as high as the dose concentration is sensed. In this case, a range of the width t of the cavity 43<11.8 mm may be set.

Moreover, for example, in a suspension culture process, subculture is generally performed in a case where the concentration of the cells is too higher. The subculture is an operation of lowering the concentration of the cells, for example. The concentration of the cells is a reference for this subculture is about 1000 cell/mm$^3$. For example, it is assumed that the mean diameter of the cells is 6 μm and culture solution including cells with a concentration (10000 cell/mm$^3$) ten times as high as the subculture concentration is sensed. In this case, sensing with the subculture concentration or the like can be properly performed by setting the width t of the cavity 43 to be 3.5 mm.

It should be noted that a method of setting the width t of the cavity 43 is not limited to the above-mentioned method. As will be described later, in this embodiment, information regarding the color of the culture solution 1 is sensed utilizing the phenomenon that the illumination light 4 is absorbed by the culture solution 1. In this case, the amount of absorption of the illumination light 4 is larger as the optical path of the illumination light in the culture solution 1 becomes longer. Further, more precise detection can be performed. Therefore, for example, the width t of the cavity 43 may be set in a manner that depends on characteristics and the like of the amount of absorption of the illumination light 4. As a matter of course, the width t of the cavity 43 may be set on the basis of both of the coherence of the illumination light 4 and the amount of absorption in the cavity 43.

Figure 6:
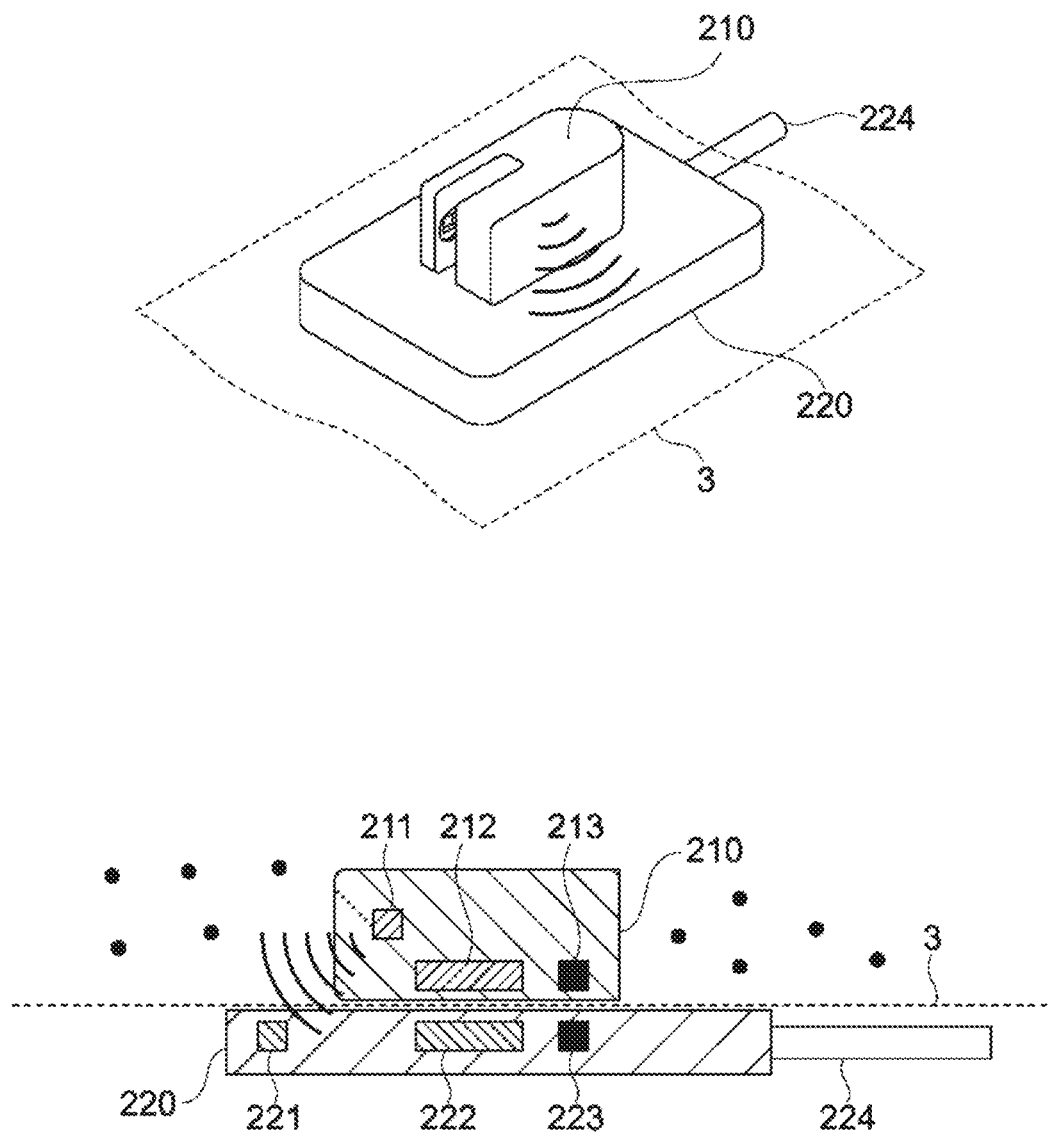
FIG. 6 A diagram for describing an example of a connection form of the measurement apparatus.

FIG. 6 is a diagram for describing an example of a connection form of the measurement apparatus. A of FIG. 6 is a perspective view of a measurement apparatus 210 arranged in the pack 3 and a power feeder/image receiver 220. B of FIG. 6 is a cross-sectional view of the measurement apparatus 210 arranged in the pack 3 and the power feeder/image receiver 220.

In the example shown in FIG. 6, the measurement apparatus 210 performs wireless communication and wireless power feeding to the external devices of the pack 3. In order to do so, the measurement apparatus 210 is used together with the power feeder/image receiver 220 located outside the pack 3.

As shown in B of FIG. 6, the measurement apparatus 210 includes a wireless communication unit 211, a wireless power feeding receiver 212, and a fixed magnet 213. The measurement apparatus 210 is arranged next to the power feeder/image receiver 220 while interposing the pack 3 therebetween.

The wireless communication unit 211 is a module for performing a short-distance wireless communication and the like with the power feeder/image receiver 220. A wireless local area network (LAN) module such as Wi-Fi or a communication module such as Bluetooth (registered trademark) is used, for example. The wireless power feeding receiver 212 is an element for receiving electric power transmitted in a contactless manner. The fixed magnet 213 is a magnet for fixing the measurement apparatus 210 to a predetermined position of the power feeder/image receiver 220.

The power feeder/image receiver 220 includes a wireless communication unit 221, a wireless power feeding transmitter 222, a fixed magnet 223, and a power feeding/communication cable 224.

The wireless communication unit 221 performs wireless communication or the like with the measurement apparatus 210. The wireless power feeding transmitter 222 supplies the measurement apparatus 210 with electric power transmitted in a contactless manner. The fixed magnet 223 fixes the measurement apparatus 210 together with the fixed magnet 213 of the measurement apparatus 210. The power feeding/communication cable 224 feeds electric power for wireless power feeding and sending/receiving of a data signal for wireless communication and the like.

For example, the wireless communication unit 211 of the measurement apparatus 210 sends image data and the like acquired by the image sensor as a wireless signal. The wireless communication unit 221 of the power feeder/image receiver 220 receives the wireless signal. The wireless communication unit 221 of the power feeder/image receiver 220 sends the image data and the like to the processing apparatus 20 and the like via the power feeding/communication cable 224 as appropriate.

By configuring the measurement apparatus 210 to be capable of wireless communication and wireless power feeding as described above, the states and the like of the cells 2 can be sensed without exposing the cells 2, the culture solution 1, and the like in the pack 3 to the external air. Accordingly, the culture step and the like of the cells 2 can be easily monitored even in a case where culture is performed with the pack 3 completely hermetically sealed, in a case where culture it is difficult to perform wiring, or the like.

Figure 7:
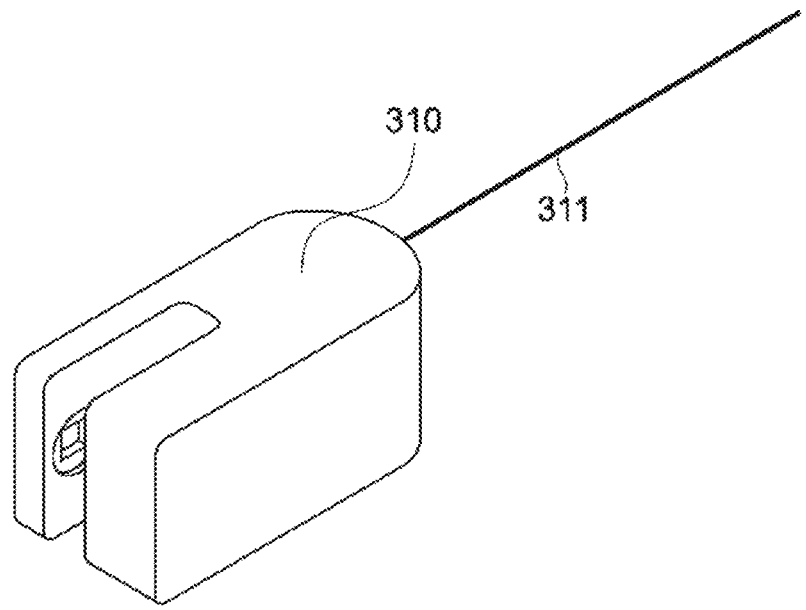
FIG. 7 A perspective view for describing another example of the connection form of the measurement apparatus.

FIG. 7 is a perspective view for describing another example of the connection form of the measurement apparatus. In FIG. 7, a measurement apparatus 310 includes a power-feeding/communication cable 311 and is wiredly connected to the external devices of the pack 3. For example, in a case where introduction and the like of wires to a culture apparatus and the like can be performed, the measurement apparatus 310 including the power-feeding/communication cable 311 can be used. Accordingly, for example, the number of components of the apparatus can be reduced. A small and inexpensive apparatus can be thus provided.

Referring back to FIG. 1, the processing apparatus 20 includes hardware necessary for computer configurations such as a central processing unit (CPU), a read only memory (ROM), a random access memory (RAM), and a hard disk drive (HDD). The personal computer (PC) is used as the processing apparatus 20, for example. Alternatively, any other computer may be used.

By the CPU loading a program according to the present technology, which is stored in the ROM or HDD, into the RAM and executing the loaded program, the acquisition unit 21, the calculation unit 22, and the display controller 23 which are the functional blocks shown in FIG. 1 are realized. Then, those functional blocks execute an information processing method according to the present technology. It should be noted that dedicated hardware may be used as appropriate in order to realize the respective functional blocks. In this embodiment, the processing apparatus 20 corresponds to an information processing apparatus.

The program is installed in the processing apparatus 20 via various recording media, for example. Alternatively, the program may be installed via the Internet or the like.

The acquisition unit 21 acquires the image data in which the interference fringes of the illumination light 4 passing through the liquid including the cells 2 are recorded. The acquisition unit 21 acquires image data generated by the image sensor 14 via the control unit 15 of the measurement apparatus 10, for example. The acquired image data is output to the calculation unit 22.

The calculation unit 22 performs propagation calculation on the illumination light 4 on the basis of the image data, to thereby calculate the cell information regarding the cells 2. Moreover, the calculation unit 22 calculates culture solution information regarding the culture solution 1 on the basis of the image data. An operation of the calculation unit 22 will be described later in detail. In this embodiment, the culture solution information corresponds to liquid information.

The display controller 23 controls display of the monitoring image 50 indicating a temporal change in the cell information. The display controller 23 is, for example, capable of acquiring the cell information and the culture solution information calculated by the calculation unit 22 and controlling the contents and the like displayed on the monitoring image 50 on the basis of such information. The monitoring image 50 is output to the display apparatus 30 via an output interface (not shown).

The display apparatus 30 is a display device using crystal liquid, electro-luminescence (EL), or the like, for example. The monitoring image 50 and the like output from the processing apparatus 20 are displayed on the display apparatus 30. A user refers to the monitoring image 50 and the like displayed on the display apparatus 30, for example, to thereby easily sense the states and the like of the cultured cells 2 in real time.

Figure 8:
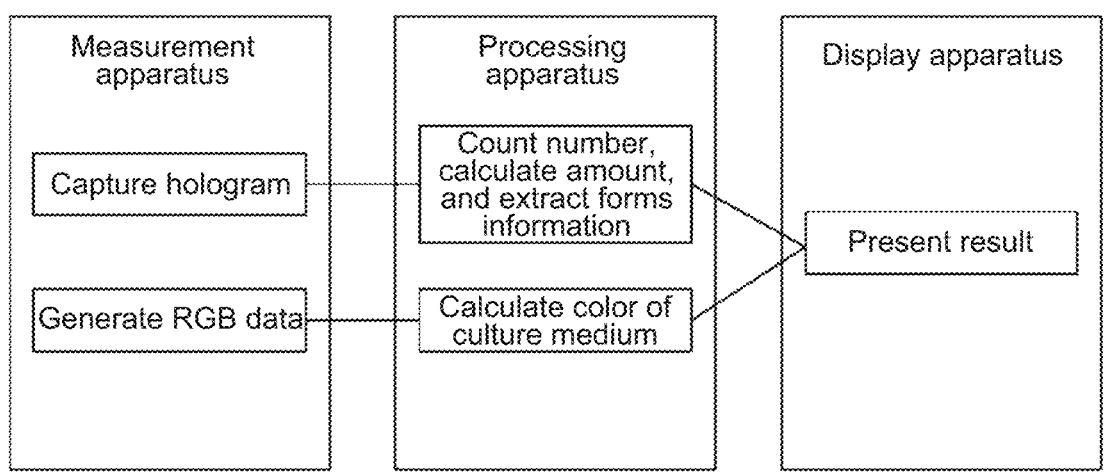
FIG. 8 A diagram for describing a basic operation example of the measurement system.

FIG. 8 is a diagram for describing a basic operation example of the measurement system 100. As shown in FIG. 8, the measurement apparatus 10 captures a hologram of the cells 2 floating in the culture solution 1. The hologram of the cells 2 is an interference pattern (interference fringes) of the illumination light 4 on the detection surface 16, which is produced when the illumination light 4 is diffracted by the cells 2. Therefore, detecting the interference fringes through the image sensor 14 includes capturing the hologram of the cells.

It should be noted that the illumination light 4 having a predetermined wavelength is used in capturing the hologram. For example, any one of red light R, green light G, or blue light B which can be emitted by the light source 12 is used as the illumination light 4. As a matter of course, the illumination light 4 is not limited thereto. For example, the wavelength used for capturing the hologram may be set as appropriate in a manner that depends on the resolution of the image sensor 14, the sizes of the cells 2 to be targets, and the like.

The captured hologram is output to the processing apparatus 20 as image data. At the processing apparatus 20, the calculation unit 22 calculates cell information regarding the cells 2 on the basis of the image data (hologram of the cells 2). The calculation unit 22 counts the number of cells 2, calculates the amount of cells 2, and extracts forms of cells 2. The calculation unit 22 calculates the number of cells 2, the concentration, the size, and the shape as cell information.

Moreover, as shown in FIG. 8, in the measurement apparatus 10, the image sensor 14 generates a plurality of pieces of image data corresponding to each of light beams having wavelengths different from each other. Specifically, the image sensor 14 generates each of red image data, green image data, and blue image data corresponding to each of the red light R, the green light G, and the blue light B. Hereinafter, the plurality of pieces of image data corresponding to respective RGB-color light beams will be collectively referred to as RGB data in some cases.

At the processing apparatus 20, the acquisition unit 21 acquires a plurality of pieces of image data (RGB data) respectively corresponding to a plurality of light beams having wavelengths different from each other, which are emitted by the light source 12 of the measurement apparatus 10 as the illumination light 4. Then, the calculation unit 22 calculates, on the basis of the plurality of pieces of image data, the color information of the culture solution 1 including the cells 2 as the culture solution information. That is, the calculation unit 22 calculates a color of the culture solution. In this embodiment, the calculation unit 22 functions as a color-information calculation unit.

At the processing apparatus 20, the display controller 23 controls the contents and the like of the display of the monitoring image 50 on the basis of the cell information and the color information (culture solution information) of the culture solution 1. Then, the monitoring image 50 is presented as a result of sensing by the display apparatus 30. It should be noted that the timing and the like for controlling the display of the monitoring image 50 are not limited. For example, the monitoring image 50 may be updated as appropriate in a manner that depends on the timing and the like at which the hologram or the RGB data is acquired.

In this manner, a processing for calculating the cell information and a processing for calculating the color of the culture solution are performed at the measurement system 100. Hereinafter, each of the types of processing will be described specifically.

[Calculation Process for Cell Information]

Figure 9:
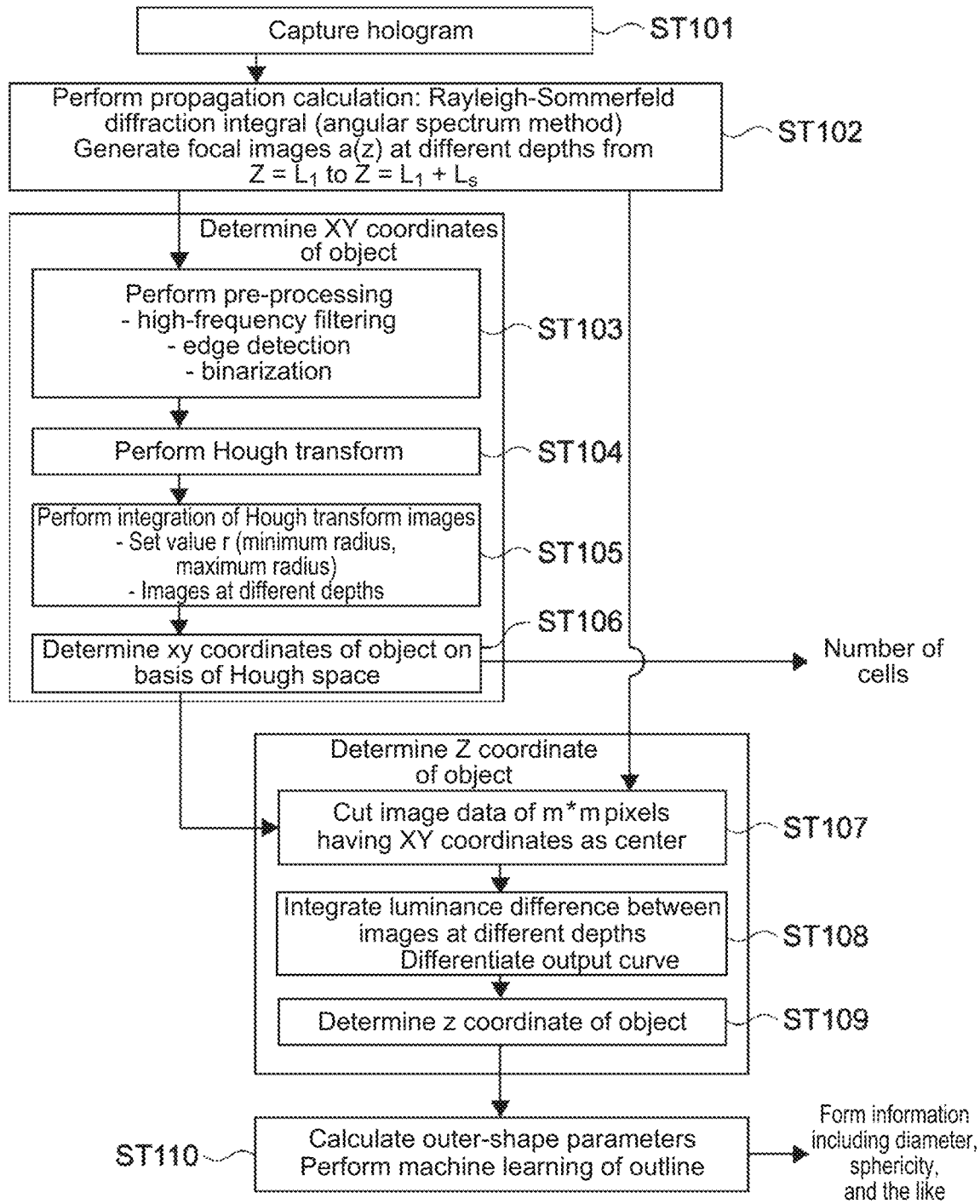
FIG. 9 A flowchart showing an example of a processing for calculating cell information.

FIG. 9 is a flowchart showing an example of the processing for calculating cell information. First of all, the hologram of the cells 2 is captured and the acquisition unit acquires the captured hologram as image data (Step 101)

The calculation unit 22 performs propagation calculation on the illumination light 4 on the basis of the acquired image data (Step 102). In this embodiment, Rayleigh-Sommerfeld diffraction integral (angular spectrum method) is performed as the propagation calculation on the illumination light 4. It should be noted that a method and the like to be used for light propagation calculation are not limited. For example, a approximate formula of Fresnel approximation, Fraunhofer approximation, or the like may be used for propagation calculation. Additionally or alternatively, an arbitrary method by which propagation calculation can be performed may be used.

Figure 10:
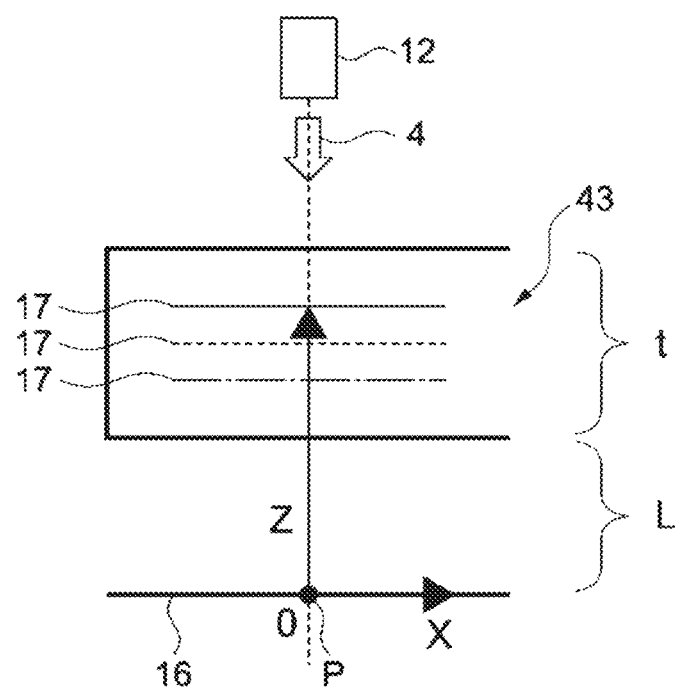
FIG. 10 A schematic view showing an arrangement relationship between the detection surface and a cavity in propagation calculation.

FIG. 10 is a schematic view showing an arrangement relationship between the detection surface 16 and the cavity 43 in propagation calculation. FIG. 10 schematically shows the light source 12, the cavity 43, and the detection surface 16. It should be noted that illustration of the collimator lens 13, the first optical window 46, and the second optical window 47 described in FIG. 3 are omitted from FIG. 10.

Hereinafter, the description will be made assuming that a point P at which the optical axis O intersects with the detection surface 16 is a point of origin in the Z axis direction and a direction toward the cavity 43 from the detection surface 16 is a positive direction of the Z axis direction. Moreover, directions perpendicular to the Z axis direction and orthogonal to each other will be referred to as an X axis direction and a Y axis direction. The X axis direction and the Y axis direction correspond to a vertical direction and a horizontal direction of the detection surface 16, for example. In FIG. 10, a direction in which the first and second projections 41 and 42 project from the base portion 40 (see FIG. 3) is set as a positive direction of the X axis direction.

The calculation unit 22 calculates a plurality of pieces of focal image data by propagation calculation on the illumination light 4. The plurality of pieces of focal image data respectively correspond to the plurality of focal planes 17 which through the illumination light 4 passes in the culture solution 1 including the cells 2. As shown in FIG. 10, the focal planes 17 are set inside the cavity 43, for example, to be orthogonal to the optical-path direction (Z axis direction) of the illumination light 4.

In FIG. 10, a distance between the detection surface 16 and the second surface 45 is set as L. Therefore, a position z of the focal plane 17 in the Z axis direction is set such that L<z<L+t is established. It should be noted that the number of focal planes 17, the positions of the focal planes 17, and the like are not limited. For example, the number of focal planes 17, the positions of the focal planes 17, and the like may be set as appropriate such that the cell information can be calculated with desired precision.

For example, an intensity distribution of the illumination light 4 when passing through the focal planes 17 can be calculated by performing propagation calculation on the focal planes 17 on the basis of an intensity distribution (interference fringes) of the illumination light 4 generated on the detection surface 16. Accordingly, the states and the like of the cells 2 present on the focal planes 17 can be specifically sensed.

The calculation unit 22 performs propagation calculation on each focal plane 17 on the basis of the image data. The calculation unit 22 calculates each of calculation results of propagation calculation as pieces of focal image data. That is, the calculation unit 22 is capable of calculating, on the basis of the single piece of image data, pieces of focal image data on the plurality of focal planes 17 at different depths in the Z axis direction. Accordingly, approximately all the cells 2 included in the cavity 43 (detection space 48) can be sensed in a single capture.

Hereinafter, the focal image data generated on the focal plane 17 at the position z will be referred to as a (x, y, z). It should be noted that a (x, y, 0) represents a data image (hologram) detected by the image sensor 14. In this embodiment, the focal plane 17 corresponds to an intermediate plane and the focal image data corresponds to intermediate image data.

Figure 11A:
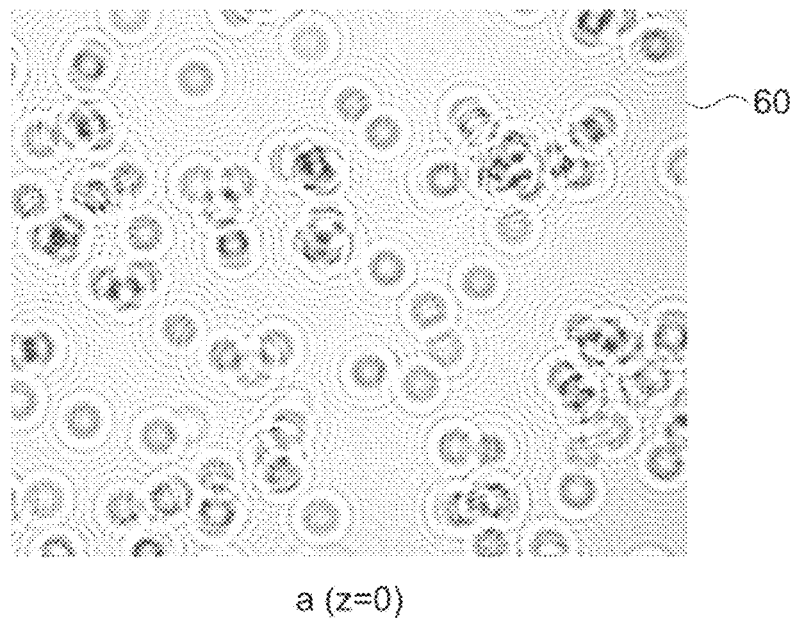
FIGS. 11A and 11B A diagram showing image data to be used for propagation calculation and a calculation result of propagation calculation.
Figure 11B:
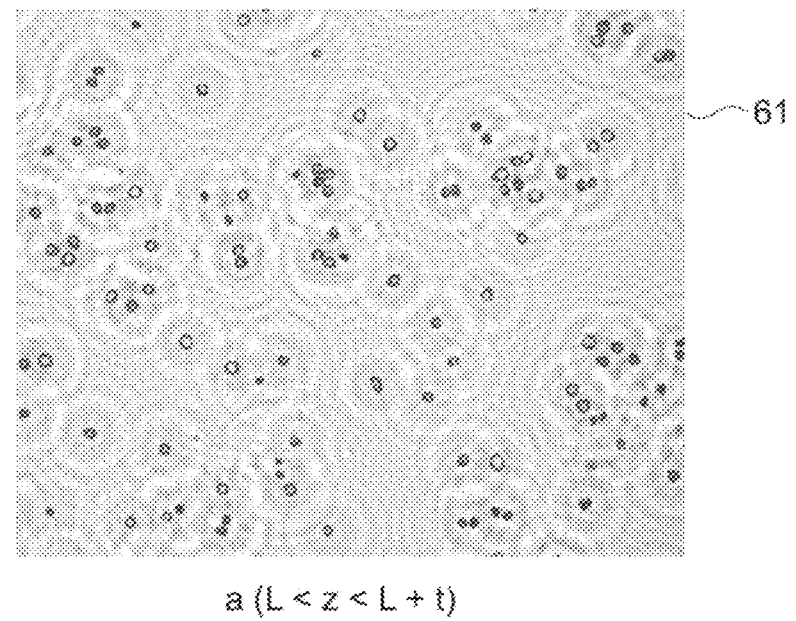

FIGS. 11A and 11B are diagrams showing image data to be used for propagation calculation and a calculation result of propagation calculation. FIG. 11A is an image 60 constituted by the image data. FIG. 11B is an image 61 constituted by focal image data calculated on the basis of the image data shown in FIG. 11A.

As shown in FIG. 11A, the interference fringes (hologram) of the illumination light 4 diffracted by the cells 2 are recorded in the image data. The hologram obtained from the particle-like cells 2 includes the concentric circular light and dark lines. For example, with respect to the single cell 2, a concentric circular light and dark line (interference fringe) having the position of that cell as a reference is detected. Assuming that this concentric circular light and dark line is a single group, the number of such groups corresponds to the number of cells 2 floating in the culture solution 1.

As shown in FIG. 11B, the focal image data includes information regarding the position, the size, and the shape (outline), and the like of each of the individual cells 2 on the focal plane 17. For example, each cell on the focal plane 17 can be specifically sensed by analyzing the focal image data. It should be noted that a ring-like artifact or the like along with propagation calculation appears around each cell 2. Therefore, the image 61 constituted by the focal image data becomes a ringing image in which an object (cell 2) is surrounded by a light and dark pattern.

Figure 12:
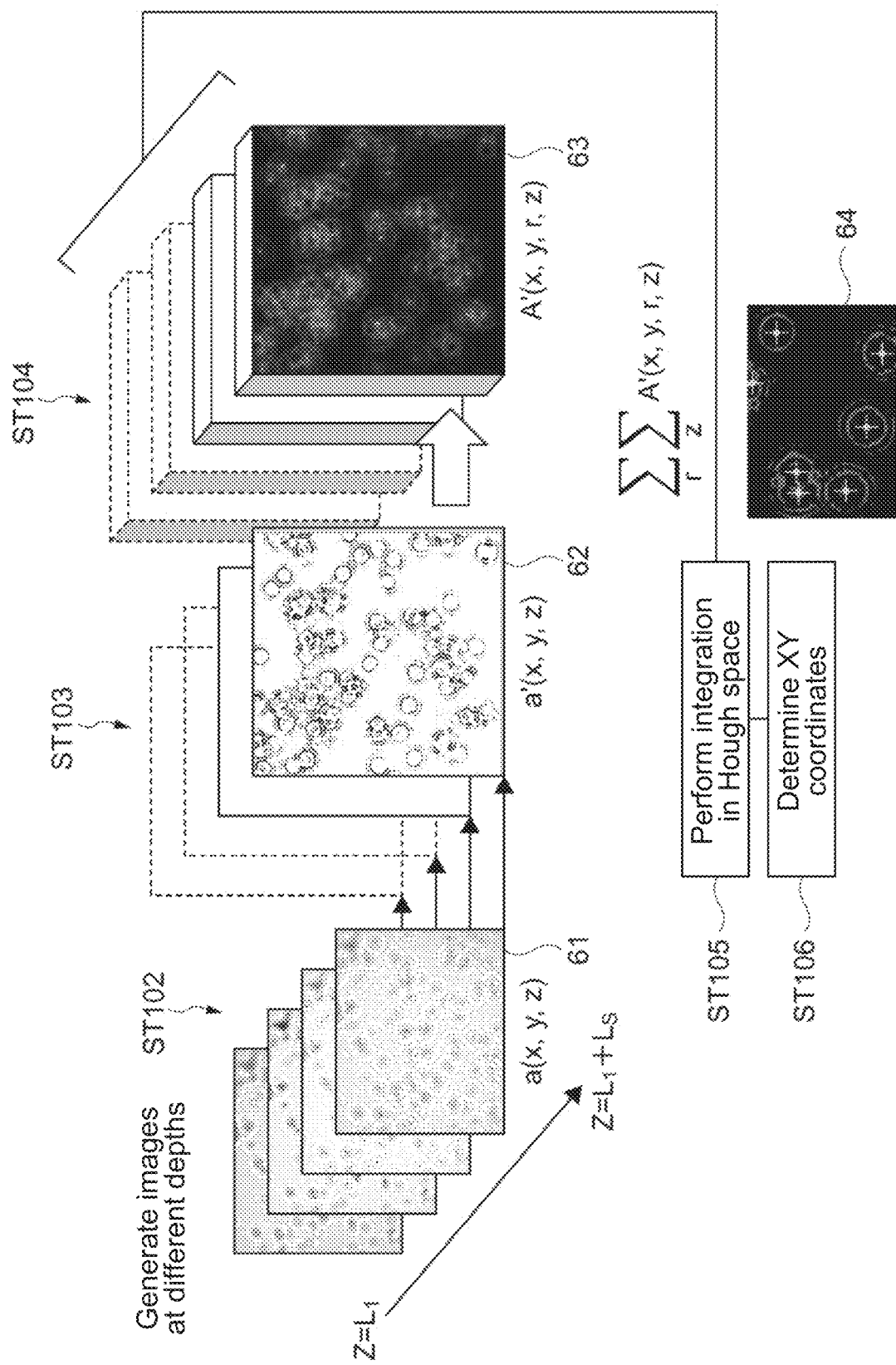
FIG. 12 A diagram for describing an example of a processing of calculating XY coordinates of a cell.

Referring back to FIG. 9, when the focal image data on each focal plane 17 is calculated, a processing of calculating XY coordinates of the cell 2 (Steps 103 to 106) is started. FIG. 12 is a diagram for describing an example of the processing of calculating the XY coordinates of the cell 2. Hereinafter, the processing of calculating the XY coordinates of the cell 2 will be described with reference to FIGS. 9 and 12.

First of all, pre-processing is performed on each of the plurality of pieces of focal image data (Step 103). In the pre-processing, the image filter filters a space frequency component having a high frequency which is included in each piece of focal image data. As a result, fine noise components and the like are removed. Moreover, outlines of the cells 2, surrounding rings, and the like are detected by edge detection processing. The detected sites (the cells 2, the rings, and the like) are binarized as white and black data from a gray scale.

In Step 103, image data a'(x, y, z) after the pre-processing is calculated with respect to each piece of focal image data. FIG. 12 shows an example of an image 62 obtained by the pre-processing. It should be noted that the processing contents of the pre-processing are not limited. For example, various types of processing of dark level correction, inverse gamma correction, up-sampling, end-portion processing, and the like may be performed as appropriate.

The Hough transform is performed on the image data a' (x, y, z) after the pre-processing (Step 104). The Hough transform is transform processing for detecting a predetermined shape inside the image. In this embodiment, the Hough transform for detecting a circle passing through a point on an edge detected by the pre-processing is performed. In the Hough transform for detecting the circle, a parameter r regarding a radius of the circle is used.

By the Hough transform, the image data a'(x, y, z) is transformed into a Hough transform image A'(x, y, z, r). The Hough transform image A'(x, y, z, r) is an image to be used in detection of a circle having a radius r. FIG. 12 shows an example of a Hough transform image 63 generated by the Hough transform. For example, in the Hough transform image 63, a value (light and dark) of each position represents candidates of center coordinates of the circle having the radius r in the image data a' (x, y, z). That is, a bright portion in the Hough transform image 63 is a portion as a likely candidate of the center coordinates.

The calculation unit 22 calculates a plurality of Hough transform images 63 within a search range having the radius r. The search range having the radius r is set in advance. The search range is expressed as $r_{min} \leq r \leq r_{max}$ using a minimum radius $r_{min}$ and a maximum radius $r_{max}$ of the radius r, for example. A plurality of times of Hough transform respectively corresponding to a plurality of radiuses r falling within this search range is performed. Therefore, the image data a' (x, y, z) is transformed into three-dimensional data (data of a Hough space) as shown in FIG. 12. It should be noted that the Hough transform processing is performed on each of pieces of image data a'(x, y, z) corresponding to the respective focal planes 17.

The minimum radius $r_{min}$ of the search range is set in accordance with the sizes of the cells 2 (3 μm to 10 μm) in the culture solution 1, for example. Moreover, the maximum radius $r_{max}$ of the search range is set in accordance with the diameter (to 50 μm) of the ring around the cell of the focal image data, for example. It should be noted that the search range having the radius r is not limited. For example, the search range having the radius r may be set as appropriate in a manner that depends on time required for calculation, calculation precision, and the like.

Integration processing (integration in the Hough space) regarding the plurality of Hough transform images 63 calculated is performed (Step 105). In this embodiment, the following calculation is performed as the integration processing.

$$\sum_r \sum_z A'(x, y, r, z) \qquad \text{[Formula 1]}$$

In the integration processing, as shown in (Formula 1), values of the respective positions (x, y) of Hough transform images A'(x, y, z, r) are integrated regarding the search range having the radius r and a depth z of each focal plane. As a result, at the position (x, y) corresponding to the center coordinates of the circle (ring) that appears on each focal plane, an integration value is a higher value than those at the other positions. FIG. 12 shows an image 64 representing the integration values.

XY coordinates of an object (cell 2) is determined on the basis of the Hough space (Step 106). For example, the calculation unit calculates a position (x, y) whose integration value is larger than a predetermined threshold, as the center coordinates of the circle in the focal image data. Accordingly, XY coordinates of the cell 2 positioned at the center of the circle can be determined. As a matter of course, in a case where a plurality of positions whose integration value is larger than the threshold are present, the XY coordinates of each of the plurality of the cells 2 are determined.

In this manner, on the basis of the plurality of pieces of focal image data, the calculation unit 22 calculates a position of the cell 2 in an XY plane direction which is a plane direction perpendicular to the optical-path direction of the illumination light 4. Accordingly, for example, each of the individual cells 2 included in the culture solution 1 can be analyzed. As a result, the states of the cells 2 included in the culture solution 1 and the like can be specifically sensed.

Moreover, the calculation unit 22 calculates the number of cells 2 on the basis of the XY coordinates of the cell 2. The number of cells 2 included in the cavity 43 is calculated by counting the total number of XY coordinates of the cell 2, for example. Moreover, the concentration of the cells 2 in the culture solution 1 and the like can be calculated on the basis of the number of cells 2 and the capacity of the cavity 43 which are calculated. Information regarding the number of cells, the concentration, and the like calculated is output to the display controller.

It should be noted that not limited to the case where the XY coordinates of the cell 2 are determined using the Hough transform, an arbitrary method by which the XY coordinates can be determined may be used. The XY coordinates of the cell 2 may be determined using image recognition processing using machine learning and the like, for example. Additionally or alternatively, arbitrary image detection processing and the like may be used.

Referring back to FIG. 9, when the XY coordinates of the cell 2 are calculated, processing (Steps 107 to 109) of calculating a Z-coordinate of the cell 2 is started.

First of all, image data b (x, y, z) of m×m pixels having the XY coordinates of each cell 2 as the center is respectively cut from the focal image data a (x, y, z) on each focal plane 17 (Step 107). Accordingly, an image of an area (b (x, y, z)) in which each cell presents is extracted. The size (m×m pixels) of the image data to be cut is set as appropriate in accordance with the sizes of the cells 2 and the like which are conceivable, for example.

The calculation unit 22 cuts image data b (x, y, z) from each of respective pieces of focal image data at different depths (positions in a z axis direction) on the basis of the XY coordinates of the cell 2 which is a target, for example. Therefore, a plurality of pieces of image data b (x, y, z) is cut with respect to the single cell 2. Similar processing is also performed on the other cells 2.

With respect to each cell 2, a luminance difference between the pieces of cut image data is calculated (Step 108). A luminance difference f between the pieces of image data is given in accordance with the expression below, for example.

$$f\left(z + \frac{\Delta z}{2}\right) = \sum_x \sum_y \{b(x, y, z + \Delta z) - b(x, y, z)\} \qquad \text{[Formula 2]}$$

Where Δz is a distance between the adjacent focal planes 17. As shown in (Formula 2), the total sum of luminance differences at the respective points between adjacent b (x, y, z) and b (x, y, z+Δz) in the entire image is calculated. Accordingly, an output curve indicating how the luminance of the area including the cells 2 has been changed in the optical-path direction can be calculated. Moreover, the calculation unit 22 performs differential calculus in the z axis direction on the luminance difference f.

Figure 13A:
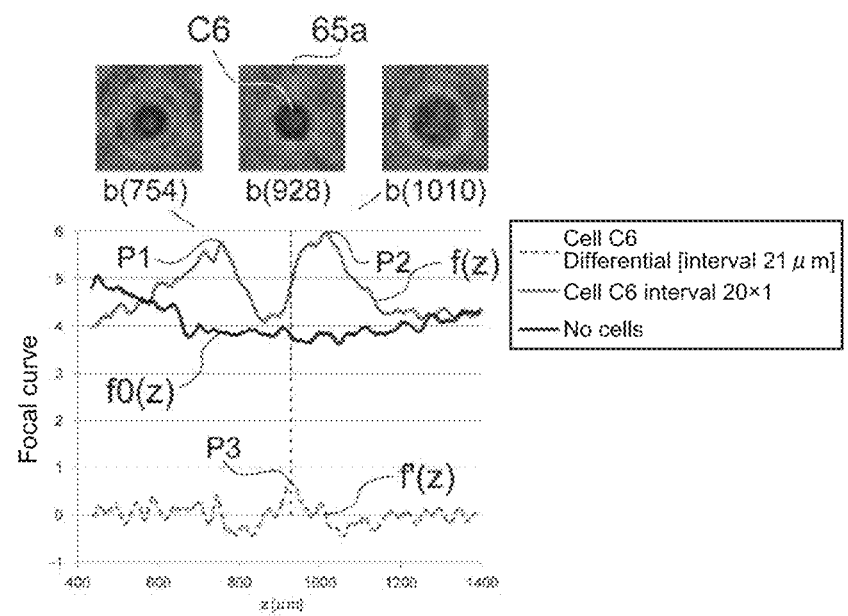
FIGS. 13A, 13B, and 13C Graphs each showing a luminance change of an area including cells in the optical-path direction.
Figure 13B:
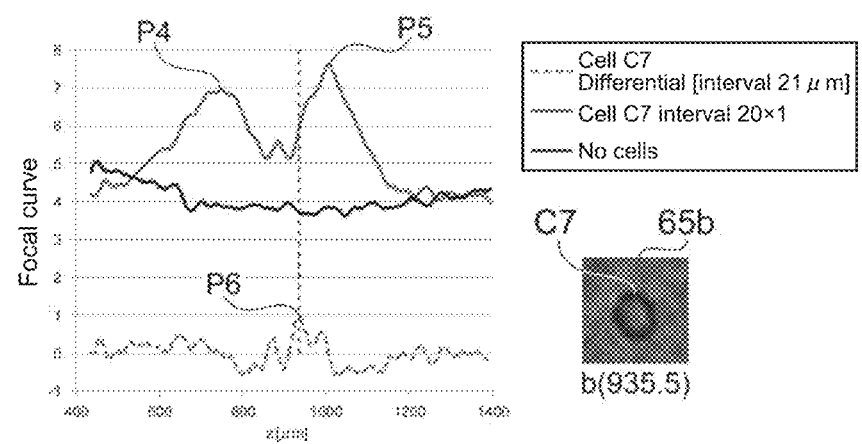
Figure 13C:
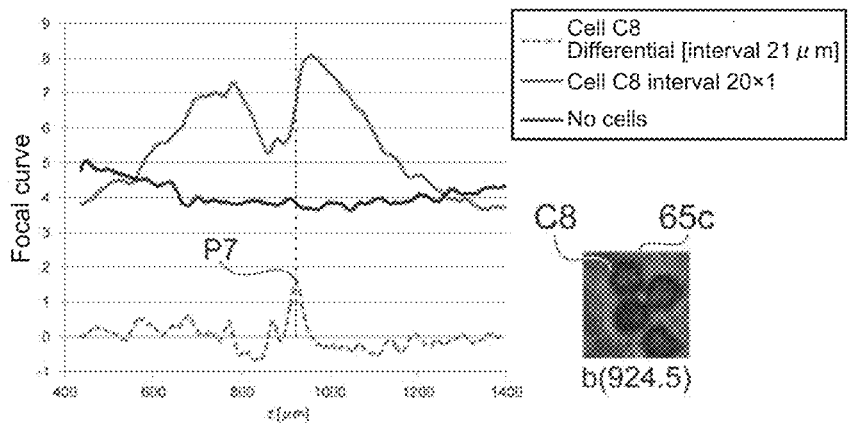

FIGS. 13A, 13B, and 13C are graphs showing a luminance change in the optical-path direction of the area including the cells 2. FIGS. 13A and 13B show graphs each indicating a luminance difference f(z) and a derivative f'(z) thereof in the areas 65a to 65c different from each other. Moreover, in of FIGS. 13A and 13B, a luminance difference f0(z) in a case where no cells 2 are present is shown. It should be noted that in FIGS. 13A, 13B, and 13C, the image data b(x, y, z) will be referred to as b(z) using the position z in the z axis direction.

FIG. 13A shows a luminance change in an area 65a including a cell C6. As shown in FIG. 13A, in the area 65a including the cell C6, the luminance difference f(z) has two peaks P1 and P2. The positions of the respective peaks P1 and P2 in the Z axis direction are respectively 754 μm and 1010 μm. Moreover, a peak P3 having the derivative f'(z) of f(z) between the two peaks P1 and P2 appears. The position of P3 in the Z axis direction is 928 μm. It should be noted that in f0(z), a clear peak is not detected.

Moreover, FIG. 13A shows image data b(754) and b(1010) of the cell 2 at the peaks P1 and P2 and image data b(928) of the cell at the peak P3. As shown in FIG. 13A, the image data b(928) at the peak P3 among the three images is a best focused image.

FIG. 13B shows a luminance change in an area 65b including a cell C7. As shown in FIG. 13B, also with respect to the cell C7, the luminance difference f(z) has two peaks P4 and P5. Moreover, a peak P6 (z=935.5 μm) of a derivative f'(z) appears between the two peaks P4 and P5. Accordingly, image data b(935.5) in which the focus is on a cell C8 can be extracted.

FIG. 13C shows a luminance change in an area 65c including a plurality of cells C8. As shown in FIG. 13B, also in a case where a plurality of cells is densely present, the graph of each of f(z) and f'(z) indicates a tendency similar to those of FIGS. 13A and 13B. That is, image data b(924.5) in which the focus is on the plurality of cells C8 can be extracted from the peak P7 (z=924.5) of f'(z).

The calculation unit 22 calculates a peak point in the derivative f'(z) of the luminance difference f (z) and determines the calculated peak point as the Z-coordinate of the cell 2 (Step 109). That is, a position at which the focus is on the cell 2 which is the target is determined as a position of that cell 2 in the Z axis direction.

In this manner, the calculation unit 22 calculates a luminance difference f (z) with respect to each of the plurality of pieces of focal image data and calculates the position of the cell 2 in the optical-path direction on the basis of the derivative f' (z) of the luminance difference f (z). Accordingly, the position (x, y, z) of the cell in the culture solution 1 is determined and each of the individual cells can be specifically sensed. In this embodiment, the luminance difference f (z) corresponds to the luminance information and the derivative f'(z) corresponds to a change in the luminance information in the optical-path direction.

It should be noted that a method of calculating a Z-coordinate of each cell 2 is not limited to the method described in Steps 107 to 109. Alternatively, any other method may be used. For example, the Z-coordinate may be determined on the basis of difference sum (luminance difference f (z)) between the respective pixels of the focal image data. Moreover, for example, a focus detection technology using machine learning may be used.

The calculation unit 22 calculates outer-shape parameters of the cell whose Z-coordinate has been calculated (Step 110). The calculation unit calculates outer-shape parameters including the sizes, the shapes, and the like of the cells 2 on the basis of the image data b(x, y, z) corresponding to the Z-coordinate of the cell 2 which is the target, for example (see FIGS. 13A, 13B, and 13C).

Outline extraction processing using machine learning or the like, for example, is performed as calculation of the outer-shape parameters. Accordingly, size-related information including the diameters and the like of the cells 2 and shape-related information including sphericity, ellipticity, and the like are calculated as the outer-shape parameters. The kinds of outer-shape parameters and the like are not limited. For example, either the size or the shape may be calculated. Alternatively, other parameters may be calculated.

It should be noted that in the focal image data, as the distance from the detection surface 16 becomes longer, i.e., the position in the Z axis direction becomes closer to the light source 12, the resolution of the image becomes lower and images and the like of the cells 2 can be blurred in some cases. In those cases, for example, processing of correcting the calculated outer-shape parameters as appropriate in view of the fact that edges of the image (outlines of the cells 2) and the like are blurred may be performed. Accordingly, the outer shape of the cell 2 can be properly detected.

[Calculation Process for Culture Solution Information]

Figure 14:
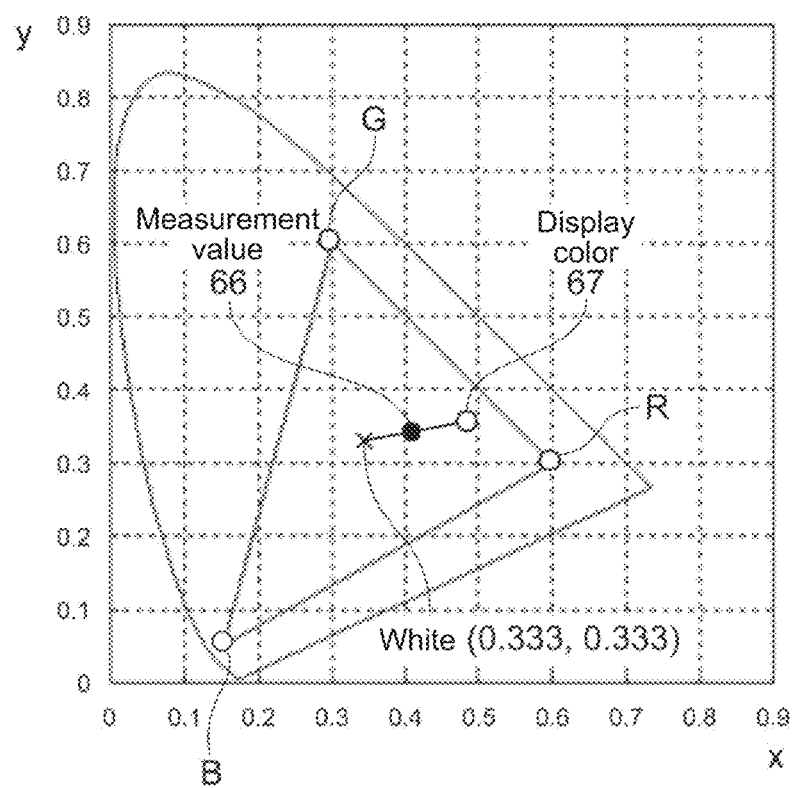
FIG. 14 A chromaticity diagram of an XYZ color space.

FIG. 14 is a chromaticity diagram of an XYZ color space. In this embodiment, the color of the culture solution 1 is represented using an XYZ color space which is a standard colorimetric system. By using the XYZ color space, the color (chromaticity) of the culture solution 1 can be calculated on the basis of a luminance of each piece of image data generated by emitting the respective RGB-color light beams, for example.

In the XYZ color space, the respective RGB-color light beams emitted from the light source 12 can be expressed as amounts called tristimulus values. For example, red light R is expressed as $[X_{R0}, Y_{R0}, Z_{R0}]$, red light G is expressed as $[X_{G0}, Y_{G0}, Z_{G0}]$, and blue light B is expressed as $[X_{B0}, Y_{B0}, Z_{B0}]$. The tristimulus values of the respective color light beams are specifically calculated as follows.

$$[X_{R0}\ Y_{R0}\ Z_{R0}] = \left[\int_\lambda \hat{R}\cdot X \quad \int_\lambda \hat{R}\cdot Y \quad \int_\lambda \hat{R}\cdot Z\right] \quad \text{[Formula 3]}$$

$$[X_{G0}\ Y_{G0}\ Z_{G0}] = \left[\int_\lambda \hat{G}\cdot X \quad \int_\lambda \hat{G}\cdot Y \quad \int_\lambda \hat{G}\cdot Z\right]$$

$$[X_{B0}\ Y_{B0}\ Z_{B0}] = \left[\int_\lambda \hat{B}\cdot X \quad \int_\lambda \hat{B}\cdot Y \quad \int_\lambda \hat{B}\cdot Z\right]$$

$$\hat{R}, \hat{G}, \hat{B} \quad \text{[Formula 4]}$$

(Formula 4) show wavelength spectra (functions of a wavelength λ) of the respective RGB-color light beams. Moreover, X, Y, Z are color functions (functions of the wavelength Λ) or the like determined in the XYZ color space. Therefore, the tristimulus values of the respective color light beams shown in (Formula 3) can be calculated by acquiring respective wavelength spectra of the red light R, the green light G, and the blue light B emitted from the light source 12 in advance, for example.

The tristimulus values of the respective color light beams shown in (Formula 3) are summed up. Accordingly, the tristimulus values expressing white light in a case where the respective RGB-color light beams are mixed and calculated.

$$[X_0 Y_0 Z_0]=[X_{R0} Y_{R0} Z_{R0}]+[X_{G0} Y_{G0} Z_{G0}]+[X_{B0} Y_{B0} Z_{B0}] \quad \text{[Formula 5]}$$

Chromaticities x0 and y0 of the white light are expressed as follows using X0, Y0, and Z0.

$$x_0 = \frac{X_0}{X_0 + Y_0 + Z_0} \quad \text{[Formula 6]}$$
$$y_0 = \frac{Y_0}{X_0 + Y_0 + Z_0}$$

In an XYZ display system, the color can be expressed by calculating the chromaticity in this manner. The color expressed by this chromaticity corresponds to the chromaticity diagram shown in FIG. 14, for example. It should be noted that the chromaticity of the white light is calculated in (Formula 6), chromaticity of each of the respective RGB-color light beams can also be calculated. FIG. 14 shows each of points corresponding to the respective RGB-color light beams.

In this embodiment, the respective RGB-color light beams are adjusted using the chromaticities x0 and y0 of the white light shown in (Formula 6). The respective RGB-color light beams are adjusted in a state in which, for example, the cavity 43 of the measurement apparatus 10 is not filled with the culture solution 1 and the like. For example, light-emitting intensities of the respective RGB-color light beams are adjusted such that the chromaticities x0 and y0 are the white color (0.333, 0.333) in the chromaticity diagram shown in FIG. 14. That is, it can also be said that the intensities of the respective color light beams emitted from the light source 12 are calibrated by using the white color as a reference.

In the measurement system 100, detection values $I_{R0}$, $I_{G0}$, and $I_{B0}$ of the image sensor 14 are recorded in advance in a state in which the chromaticity of the white light is adjusted to indicate the white color. For example, $I_{R0}$ is a mean value of luminance values of image data generated by outputting only red light in the state in which the light-emitting intensity is adjusted. Similarly, $I_{G0}$ and $I_{B0}$ are mean values of luminance values corresponding to adjusted green color light and blue color light. By using the detection values $I_{R0}$, $I_{G0}$, and $I_{B0}$ at the calibrated light source 12 in this manner, the color of the culture solution 1 and the like can be sensed with high precision.

Figure 15:
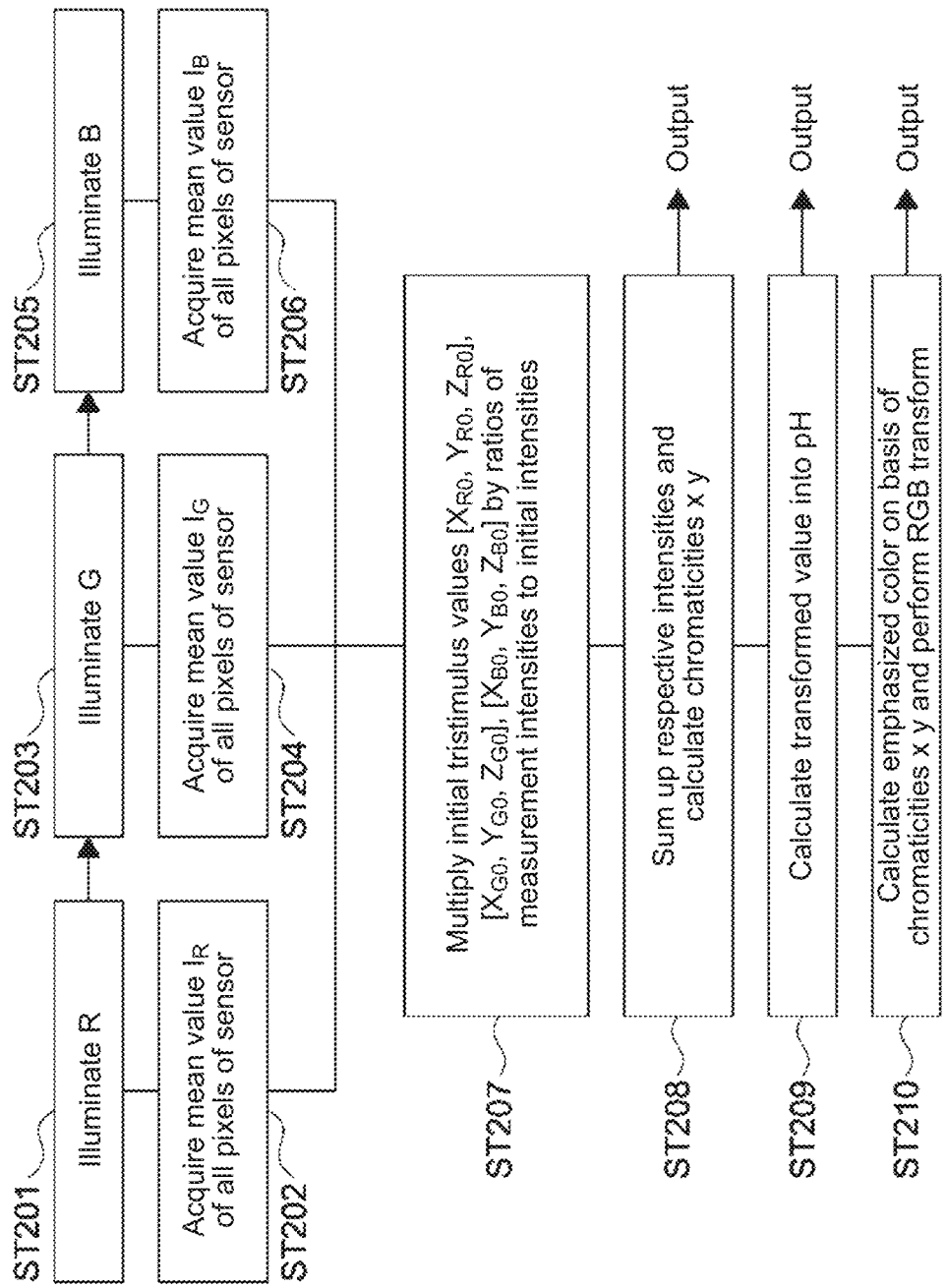
FIG. 15 A flowchart showing an example of a processing for calculating culture solution information.

FIG. 15 is a flowchart showing an example of the processing for calculating the culture solution information. In this embodiment, the processing shown in FIG. 15 is performed in the state in which the measurement apparatus 10 is put in the culture solution 1.

The light source 12 emits (illuminates) the red light R and the image sensor 14 generates the red image data (Step 201). For example, a part of the red light R entering the culture solution 1 experiences light absorption in a manner that depends on the characteristics of the culture solution 1. Moreover, another part passes through the culture solution 1.

In general, the amount of light absorbed by the culture solution 1 is an amount corresponding to the optical path length in the culture solution 1, for example. For example, light entering perpendicularly to the cavity 43 and light entering obliquely to the cavity 43 have different optical path lengths passing through the culture solution 1. In such a case, there is a possibility that different light intensities are detected.

In this embodiment, the red light R emitted from the light source 12 passes through the cavity 43 in an approximately parallel luminous flux state via the collimator lens 13 (see FIG. 3). Therefore, the optical path length when the red light R entering the detection surface 16 of the image sensor 14 passes through the inside of the culture solution 1 is approximately the same length (the width t of the cavity 43) irrespective of the position within the detection surface 16. Therefore, at each position on the detection surface 16, the transmission amount (amount of absorption) of the red light R passing through the culture solution 1 corresponding to a thickness t can be detected with high precision.

The calculation unit 22 calculates a mean value $I_R$ of luminance values of the red image data (Step 202). Accordingly, the intensity of the red light R passing through the culture solution 1 can be acquired with high precision.

The light source 12 switches the red light R to the green light G as the illumination light and generates the green image data (Step 203). The mean value $I_G$ of the luminance values are calculated on the basis of the generated green image data (Step 204). After that, the light source 12 switches the green light G to the blue light B as the illumination light and generates the blue image data (Step 205). The mean value $I_G$ of the luminance values is calculated on the basis of the generated blue image data (Step 206).

In this manner, the respective RGB-color light beams are sequentially switched and emitted. The mean of the luminance values of each of the RGB-color light beams passing through the culture solution 1 is calculated on the basis of the image data corresponding to each of the color light beams. As a matter of course, the order and the like of the color light beams to be emitted are not limited. Hereinafter, mean values ($I_R$, $I_G$, $I_B$) of the luminance values of each of the color light beams passing through the culture solution 1 will be referred to as measurement intensities and mean values ($I_{R0}$, $I_{G0}$, $I_{B0}$) of the luminance values of the light source 12 will be referred to as initial intensities in some cases.

The tristimulus values ($X_{RGB}$, $Y_{RGB}$, $Z_{RGB}$) with respect to light beams passing through the culture solution 1 are calculated on the basis of the measurement intensities ($I_R$, $I_G$, $I_B$), the initial intensities ($I_{R0}$, $I_{G0}$, $I_{B0}$), and the tristimulus values (Formula 3) of the respective RGB-color light beams (Step 207). Here, ($X_{RGB}$, $Y_{RGB}$, $Z_{RGB}$) is, for example, tristimulus values of light beams passing through the culture solution 1 in a case where the respective RGB-color light beams are mixed and emitted to the culture solution 1, i.e., the white light is emitted. Specifically, the calculation unit 22 performs the following calculation.

$$[X_{RGB}, Y_{RGB}, Z_{RGB}] = \frac{I_R}{I_{R0}}[X_{R0}, Y_{R0}, Z_{R0}] + \quad \text{[Formula 7]}$$
$$\frac{I_G}{I_{G0}}[X_{G0}, Y_{G0}, Z_{G0}] + \frac{I_B}{I_{B0}}[X_{B0}, Y_{B0}, Z_{B0}]$$

In (Formula 7), calculation of multiplying the tristimulus values of the color light beams by ratios of the measurement intensities to the initial intensities is performed with respect to the respective RGB-color light beams. As shown in (Formula 7), for example, a product of ($X_{R0}$, $Y_{R0}$, $Z_{R0}$) by $I_R/I_{R0}$ is calculated with respect to the red light R. Moreover, similar calculation is performed also with respect to the green light G and the blue light B.

In general, the light intensity absorbed by the culture solution 1 has intensities (absorption spectra) different for each wavelength. As described above, in this embodiment, the first optical window 46 and the like sharpens the spectra of the respective color light beams. A half width of the sharpened spectra of the respective color light beams is about 10 nm, for example. Therefore, the respective color light beams can be considered as light beams having an approximately single wavelength. Further, it is substantially unnecessary to consider a difference in amount of absorption and the like due to the difference in wavelength. Therefore, the light intensity when light is absorbed by the culture solution 1 can be expressed by using the ratios of the measurement intensities to the initial intensities ($I_R/I_{R0}$, $I_G/I_{G0}$, $I_B/I_{B0}$) in (Formula 7).

A chromaticity (x, y) of light absorbed by the culture solution 1 is calculated on the basis of ($X_{RGB}$, $Y_{RGB}$, $Z_{RGB}$) (Step 208). For example, as in calculation in (Formula 5), ($X_{RGB}$, $Y_{RGB}$, $Z_{RGB}$) is summed up and chromaticities x and y are calculated as follows.

$$x = \frac{X_{RGB}}{X_{RGB} + Y_{RGB} + Z_{RGB}}$$
$$y = \frac{Y_{RGB}}{X_{RGB} + Y_{RGB} + Z_{RGB}}$$
[Formula 8]

The chromaticities x and y calculated in (Formula 8) are used as a measurement value of the color of the culture solution 1. FIG. 14 schematically shows an example of the chromaticity (x, y) calculated as the measurement value as a dot 66. The calculated chromaticity (x, y) is output to the display controller 23 or the like, for example. In this embodiment, the chromaticity (x, y) of the culture solution 1 is included in color information of the liquid including the cell.

The calculation unit 22 calculates a pH value of the culture solution 1 including the cells 2 on the basis of the chromaticity (x, y) of the culture solution 1 (Step 209). As described above, a pH indicator such as phenol red is added to the culture solution 1. For example, transformed data in which a chromaticity of the culture solution 1 and a pH value of the culture solution 1 are associated with each other and the like are recorded in advance. Accordingly, for example, by referring to the transformed data, the pH value of the culture solution 1 can be easily calculated on the basis of the chromaticity of the culture solution 1. Furthermore, a method for calculating the pH value on the basis of the chromaticity is not limited. The pH value of the culture solution 1 is the culture solution information regarding the culture solution 1. In this embodiment, the liquid information includes the pH value of the culture solution 1.

The calculation unit 22 calculates a display color for displaying the color of the culture solution 1 including the cells 2 as the color information (Step 210). The display color is calculated on the basis of the chromaticity (x, y) of the culture solution 1. Moreover, the display color is transformed as a RGB value to be used in the display apparatus 30 or the like. That is, the display color of the XYZ color space is transformed into a numerical value in the RGB colorimetric system.

For example, in a case where the width t of the cavity 43 is small (e.g., to several mm), the amount of light absorption of the culture solution 1 can be small and the color specified by the chromaticity (x, y) can be a pale color. In this embodiment, a display color (white circle 67) in which the color of the culture solution 1 is emphasized is calculated by moving the measurement value (dot 66) on the xy chromaticity coordinates.

For example, the dot 66 is moved by a predetermined distance in a direction in which the dot 66 moves away from the point representing the white color along a straight line linking a point (0.333, 0.333) representing the white color to the dot 66 (x, y) as shown in FIG. 14. The point (the white circle 67) after movement is transformed into the RGB value as the point representing the display color. In this manner, in the chromaticity diagram, a darker color can be represented by moving the point on the xy chromaticity coordinates away from the white color. Accordingly, the color of the culture solution 1 can be emphasized.

It should be noted that a method of calculating the display color on the basis of the chromaticity (x, y) and the like are not limited. For example, a display color may be calculated using an arbitrary method of emphasizing the measurement value. Moreover, for example, the chromaticity (x, y) which is the measurement value may be calculated as the display color as it is. The color of the culture solution 1 can be represented with, for example, a desired hue (density, intensity, brightness, and the like) by calculating the display color for displaying the color of the culture solution 1 in this manner. After the display color is transformed into the RGB value, the RGB value is output to the display controller 23 or the like, for example. In this embodiment, the display color corresponds to display color information. Moreover, the color information includes the display color information.

In this manner, the measurement apparatus 10 and the processing apparatus 20 cooperate with each other in the measurement system 100. In this way, the cell information regarding the cells 2 and the culture solution information regarding the culture solution 1 are acquired. Those pieces of information are acquired at predetermined intervals, for example, and are used for the display control of the display controller 23 on the monitoring image 50 and the like. As a matter of course, the acquired information may be recorded in an HDD or the like and the recorded information may be referred to, as data in which the culture process is recorded.

[Display Control of Monitoring Image]

Figure 16:
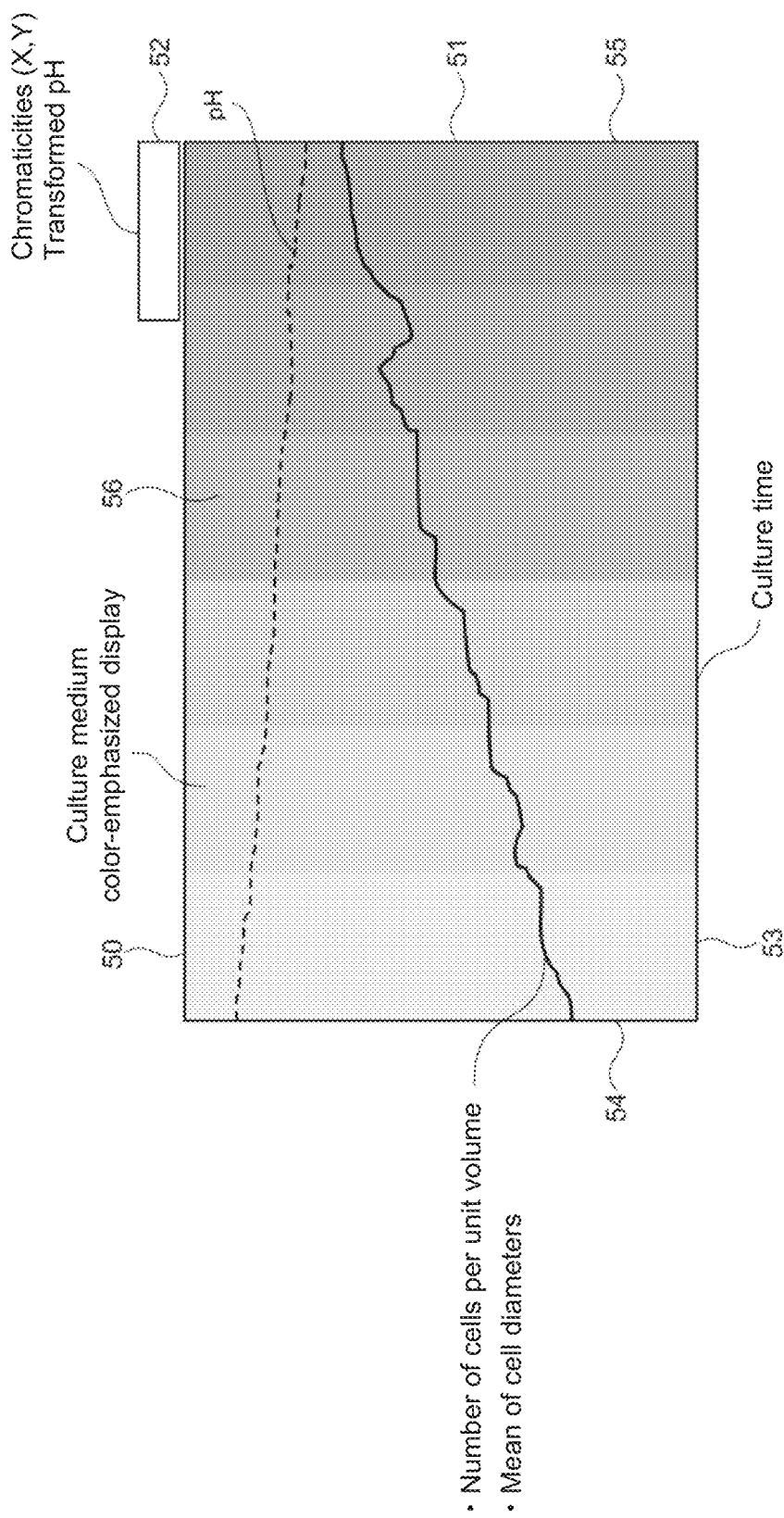
FIG. 16 A schematic view showing a configuration example of a monitoring image.

FIG. 16 is a schematic view showing a configuration example of the monitoring image 50. As described above, the display controller 23 controls the display of the monitoring image 50. In the example shown in FIG. 16, the monitoring image 50 includes a monitoring region 51 and a numerical-value display region 52.

The monitoring region 51 is a rectangular region. The monitoring region 51 includes a horizontal axis 53, a first vertical axis 54, and a second vertical axis 55. The horizontal axis 53 is set as a bottom line on a lower side of the monitoring region 51. Moreover, the first and second vertical axes 54 and 55 are set as lines on left- and right-hand sides of the monitoring region 51.

Moreover, as shown in FIG. 16, the monitoring region 51 is capable of displaying a color map 56 over the entire surface within the region. It should be noted that a color bar (not shown) and the like in which the colors of the color map 56 are made corresponding to the numerical values can be displayed in the monitoring image 50.

The monitoring image 50 includes a graph indicating a temporal change in the cell information. FIG. 16 shows a graph indicating a temporal change in the cell information by using the horizontal axis 53 of the monitoring region 51 as culture time and using the first vertical axis 54 as the cell information.

The number of cells (concentration of the cells) per unit volume of the culture solution 1, for example, is displayed as the cell information. In this case, the first vertical axis 54 indicates the number of cells. The number (concentration) of cells 2 and the like which increase over the culture time can be easily monitored. Moreover, the mean of diameters of the cells 2 may be displayed as the cell information, for example. In this case, the first vertical axis 54 indicates a mean cell diameter. How the sizes of the cells 2 have changed as the culture progresses, for example, can be easily monitored.

A type of cell information and the like to be graphed are not limited. Any type of information included in the cell information may be used. Moreover, it may be possible to switch and graph the type of cell information and the like to be displayed. For example, the display controller 23 may be capable of switching the type of cell information to be graphed on the basis of a user's instruction or the like.

Moreover, the monitoring image 50 includes a graph indicating a temporal change in the pH value of the culture solution 1. FIG. 16 shows a graph indicating a temporal change in the pH value by using the second vertical axis 55 as the pH value. Accordingly, a change in pH value and the like in the culture process can be easily monitored.

The monitoring image 50 indicates a temporal change in the culture solution information. In this embodiment, the monitoring image 50 includes a map indicating a temporal change in the color information which is the culture solution information. As described above with reference to FIGS. 14 and 15, the calculation unit 22 calculates the display color for displaying the color of the culture solution 1 as the RGB value on the basis of the chromaticity (x, y) indicating the color of the culture solution 1. The color map 56 indicating a temporal change in the display color is displayed in the monitoring image 50 by using the calculated RGB value.

In FIG. 16, the color map 56 is configured to display a temporal change in the color (display color) of the culture solution 1 along the horizontal axis 53 (culture time). For example, the color of the culture solution 1 for each time is displayed in the monitoring region 51 as gradation in which the color changes in the horizontal direction. Accordingly, for example, how the color of the culture solution 1 has changed during culture can be easily monitored. It should be noted that a specific configuration and the like of the color map 56 are not limited. For example, the color map 56 may be displayed using a part of the region of the monitoring region 51.

As shown in FIG. 16, a graph representing a temporal change in the cell information is displayed in the monitoring region 51, superimposed on the color map 56. In this manner, the display controller 23 displays each of a graph indicating a temporal change in the cell information and a map indicating a temporal change in the culture solution information in an overlapping manner. Accordingly, the state of the cells 2 and the state of the culture solution 1 can be simultaneously shown. For example, a step of culturing the cells 2 and the like can be easily monitored.

The numerical-value display region 52 is arranged near the monitoring region 51, for example. FIG. 16 shows the numerical-value display region 52 arranged in an upper right portion of the monitoring region 51. The cell information and the culture solution information are displayed as numerical values in the numerical-value display region 52. In the example shown in FIG. 16, for example, the current chromaticity (x, y) of the culture solution 1, the pH value transformed from that chromaticity (x, y) and the like are displayed with predetermined effective digit in the numerical-value display region 52.

The type of the numerical value and the like to be displayed in the numerical-value display region 52 are not limited. For example, the current concentration of the cells 2, the mean of the sizes of the cells 2 and the like may be displayed as numerical values. Moreover, for example, values (the concentration of the cells 2, the chromaticity of the culture solution 1, and the like) at each point on the graph or the map, which is instructed by the user, may be displayed in the numerical-value display region 52.

Figure 17:
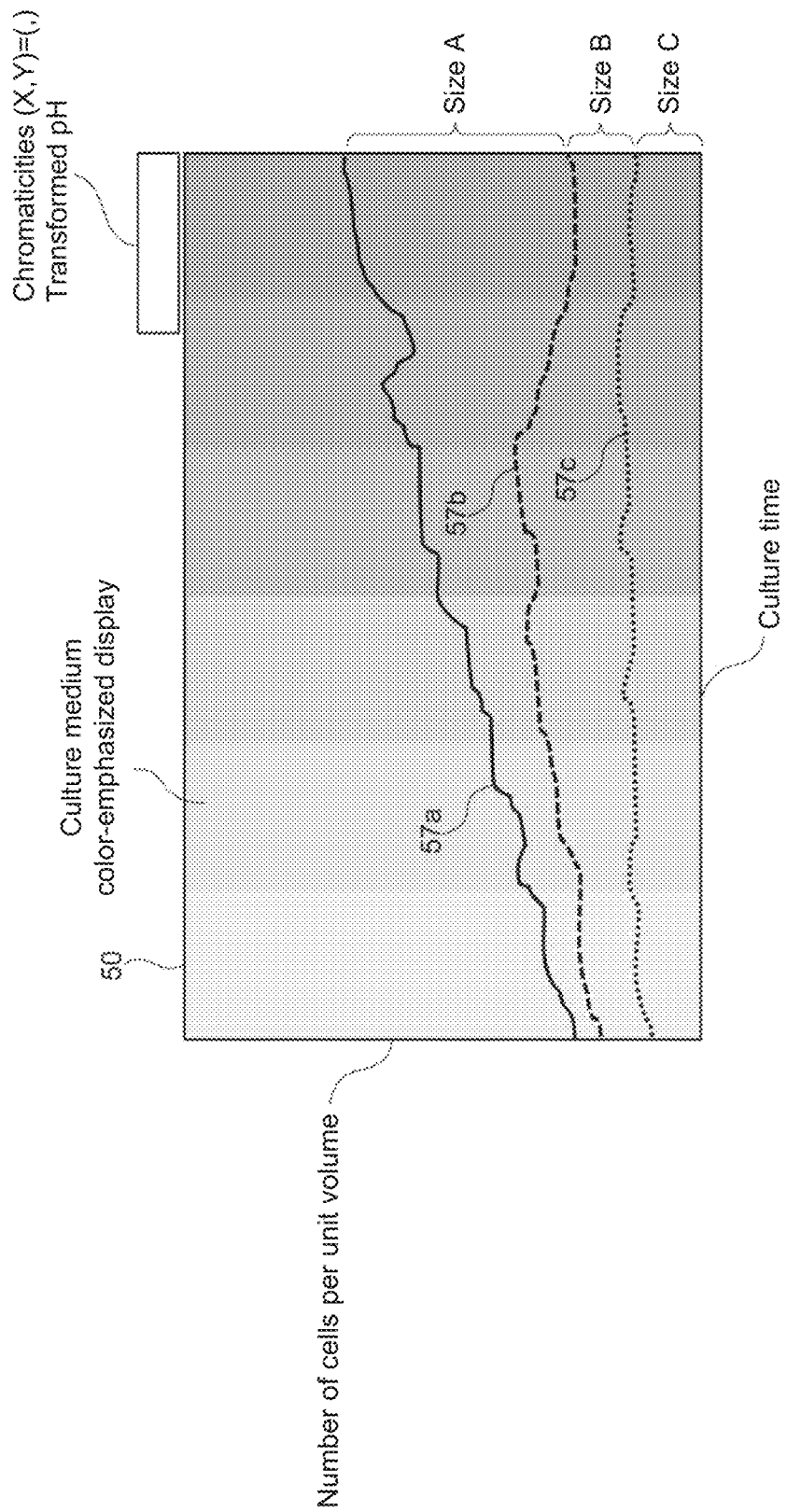
FIG. 17 A schematic view showing another configuration example of the monitoring image.
Figure 18:
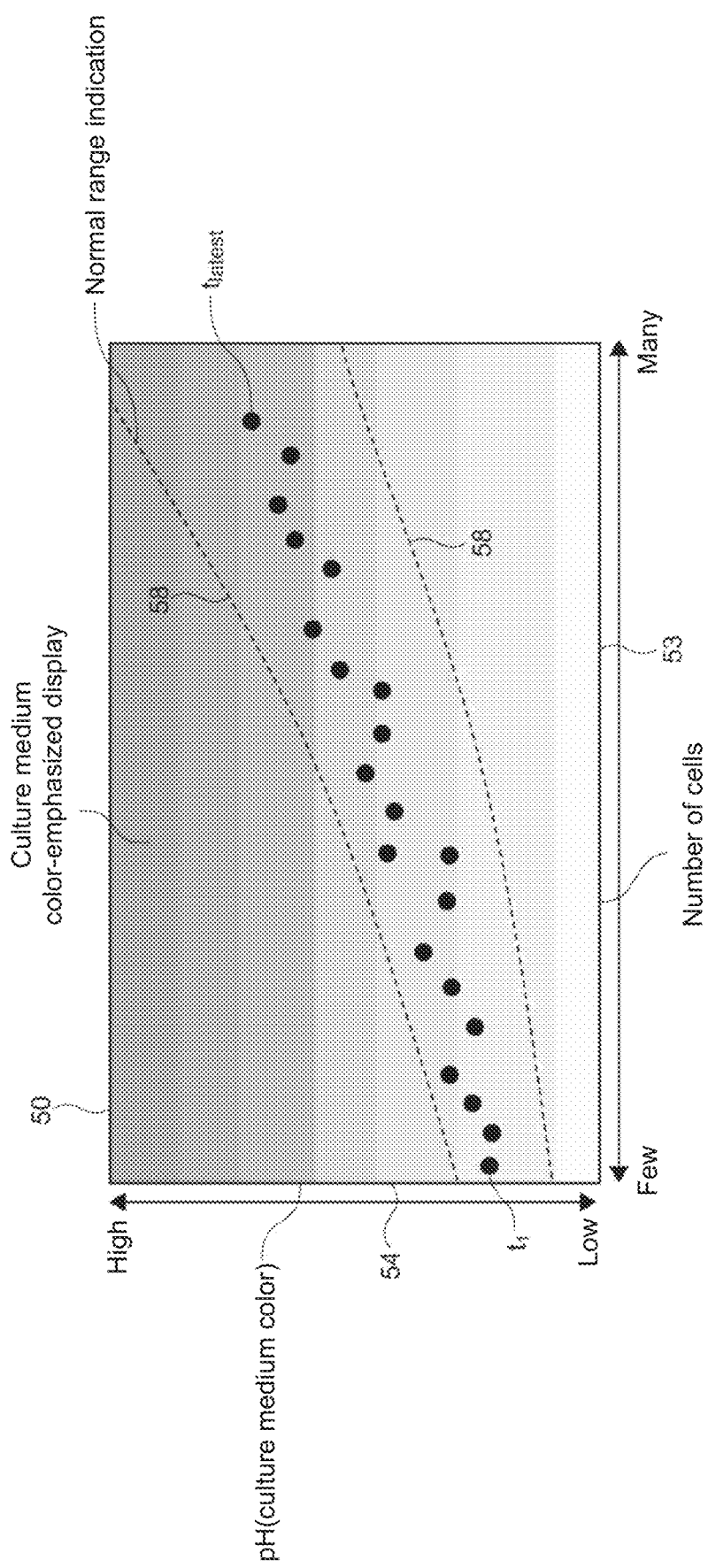
FIG. 18 A schematic view showing another configuration example of the monitoring image.

FIGS. 17 and 18 each are a schematic view showing another configuration example of the monitoring image 50. FIG. 17 shows a temporal change in the number of cells for each size with respect to the cells 2 having sizes A to C different from each other. A graph 57c indicates the number of cells 2 having the size C. A graph 57b indicates the number of cells 2 having the size C and the size B. A graph 57a indicates a total number of cells 2 (total sum of cells having the size A, the size B, and the size C).

The percentage of the sizes of the cells 2 which increases and the like can be easily monitored by displaying the graphs 57a to 57c in this manner. Accordingly, the states of the cells 2 and the like can be sensed in detail and advanced monitoring can be achieved.

In FIG. 18, the number of cells is set as the horizontal axis 53 of the monitoring region 51. Moreover, the pH value is set as the first vertical axis 54. Moreover, the color map 56 indicating the color of the culture solution 1 is displayed as gradation which changes along the first vertical axis 54 in the monitoring region 51. In this case, the color of the color map 56 is set corresponding to the pH set on the first vertical axis 54.

The display controller 23 plots respective data points acquired during culture time by using the number of cells as the horizontal axis and using the pH value as the vertical axis. For example, a data point $t_1$ in FIG. 18 indicates the number of cells and the pH value in the initially acquired data. Moreover, a data point $t_{latest}$ indicates the latest number of cells and the pH value. Even if the pH values at the respective data points are plotted with respect to the number of cells in this manner, how the cell state has changed, i.e., a temporal change in the cell information can be indicated.

Moreover, the display controller 23 displays a normal range 58 within which a temporal change in the cell information is normal on the monitoring image 50. FIG. 18 schematically shows the normal range 58 as dashed lines. The normal range 58 is calculated by using data regarding cell culture and the like carried out in the past, for example.

For example, if the data points fall within the scope of the normal range 58, the cells 2 are normally grown up. Moreover, if the data points depart from the normal range 58, it means that growing conditions of the cells 2 are not normal. By indicating the states and the like of the cells 2 together with the normal range 58 in this manner, an abnormality and the like at the culture step can be easily monitored. Accordingly, the monitoring work can be sufficiently assisted.

Hereinabove, in the measurement system 100 according to this embodiment, the cavity 43 sandwiched by the first and second surfaces 44 and 45 opposite to each other is provided on the optical path of the illumination light 4 emitted from the light source 12. This cavity 43 is filled with the culture solution 1 including the cells 2. Then, the interference fringes of the illumination light 4 which are caused by the culture solution 1 including the cells 2, which fills the cavity 43, are detected. Accordingly, the states of the cells 2 and the like can be easily sensed in real time on the basis of the interference fringes.

A method using an optical microscope and the like is conceivable as a method of sensing the states of the cells, the culture medium, and the like. In a case where the optical microscope is used, it is generally necessary to mechanically change the focus and perform shooting several times for shooting an object outside the depth of field. For example, in suspension-type cell culture using the liquid culture medium and the like, the culture medium is agitated and particles (cells, and the like) which are objects to be shot are constantly moving. Therefore, it is difficult to shoot all the particles at different positions (Z coordinates) in the depth direction. There is thus a possibility that suitable sensing cannot be performed.

For example, the cells and the like can be sensed by arranging the cells included in the liquid culture medium in a plane of a cell counter or the like. In this case, an operation and the like for extracting the liquid culture medium are necessary. Moreover, in a case where the cells floating in the liquid culture medium are directly observed, it is necessary to design dedicated culture vessel and flow channel, which can increase the cost.

In the measurement apparatus 10 according to this embodiment, the cavity 43 which can be filled with the culture solution 1 is provided. Then, a hologram (interference fringes) of the illumination light 4 passing through the cavity 43, which is caused by the culture solution 1 including the cells 2, is detected by the image sensor 14. The respective cells 2 included in the cavity 43 can be sensed on the basis of this hologram.

For example, the focal image data on the focal planes 17 at positions different from each other in the Z axis direction can be generated on the basis of the detected hologram. Accordingly, approximately all the cells 2 included in the cavity 43 can be sensed in a single capture. As a result, even with the suspension-type culture in which the cells 2 are constantly moving, states of cells and the like can be sensed in real time.

Moreover, the measurement apparatus 10 is configured such that the measurement apparatus 10 can be put inside the culture solution 1. Therefore, the number of cells and the like can be sensed in real time without taking out the culture solution 1. Moreover, the measurement apparatus 10 can be used for various culture vessels such as the pack 3 for culturing. Therefore, the cost required for sensing the cells 2 and the like can be sufficiently reduced by using the measurement apparatus 10.

The operation of acquiring the culture solution 1 in this manner is unnecessary. Therefore, the risk of contamination and the like of the culture medium due to contamination of the culture solution 1, for example, can be avoided. Accordingly, the reliability of the culture step remarkably increases. Further, the measurement apparatus 10 is capable of automatically acquiring information regarding the cells 2 and the like and easily monitoring the states of the cells 2 and the like.

Moreover, in the measurement system 100 according to this embodiment, interference fringes of the illumination light 4, which are caused by the culture solution 1 including the cells 2, are acquired as the image data. On the basis of the acquired image data, propagation calculation of the illumination light 4 is performed and the cell information is calculated. Then, the display of the monitoring image 50 indicating a temporal change in the cell information is controlled. The states of the cells 2 and the like can be easily sensed in real time by referring to the monitoring image 50.

The interference fringe (hologram) caused by the particle (cell) includes a concentric circular diffraction image. A method of performing image processing on a detected hologram and counting center coordinates of diffraction image, for example, is conceivable as a method of counting the number of particles. In this method, for example, it can be difficult to properly count the number of particles in a case where the particles come closer and diffraction images overlap each other, for example.

In the processing apparatus 20 according to this embodiment, the acquisition unit 21 acquires the image data in which the interference fringes of the illumination light 4, which are caused by the culture solution 1 including the cells 2, are recorded. The calculation unit 22 performs propagation calculation of the illumination light 4 on the basis of the image data and generates focal image data on each of focal planes 17 arranged on the optical path. By using pieces of focal image data (in-line holograms) arranged in line in this manner, the states and the like of the cells 2 can be sensed with high precision.

For example, the position of each cell 2 can be calculated with high precision by using the plurality of pieces of focal image data. Accordingly, the number of cells 2 included in the cavity 43 can be counted with high precision. Moreover, the size, the shape, and the like of each cell 2 can be detected with high precision by using the focal image data in which focusing is achieved on each cell 2, for example. Sensing of the cells 2 and the like can be achieved with sufficiently high precision by using such digital focus.

Moreover, in this embodiment, the display controller 23 controls the display of the monitoring image indicating a temporal change in the cell information. Accordingly, a temporal change in the cell information can be easily monitored in real time and advanced manufacturing control can be achieved.

For example, in the field of cell therapy, a method of performing spheroidization on the cells 2 and returning the cells 2 inside the body has been studied. In the spheroidization, the cells 2 are three-dimensionally arranged. Growth of spheroids can be monitored in real time in a case of mass-producing spheroids by rotational suspension culture or the like, for example, by using this measurement system 100.

Information which enables the pH of the culture solution 1 and the cell concentration to be simultaneously checked is displayed in the monitoring image 50. Accordingly, an operator easily recognizes an abnormality. Moreover, the parameters (the pH value of the culture solution 1, the concentration of the cells 2, and the like) which are important for keeping a production condition for the cells 2 stable by using a computer and the like can be provided. Accordingly, significantly advanced manufacturing control can be performed.

Other Embodiments

The present technology is not limited to the above-mentioned embodiment and various other embodiments can be made.

In the above-mentioned embodiment, the measurement apparatus is put in the culture solution. The present technology is not limited thereto. For example, the present technology is also applicable even in a case where the measurement apparatus is put outside the culture solution.

Figure 19A:
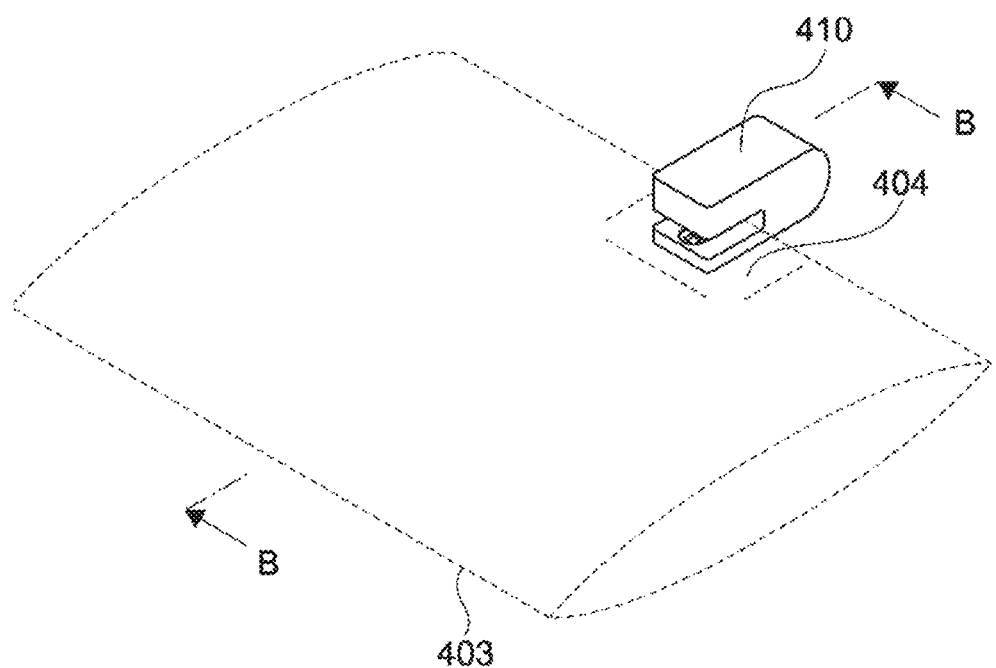
FIGS. 19A and 19B A diagram for describing an arrangement example of the measurement apparatus.
Figure 19B:
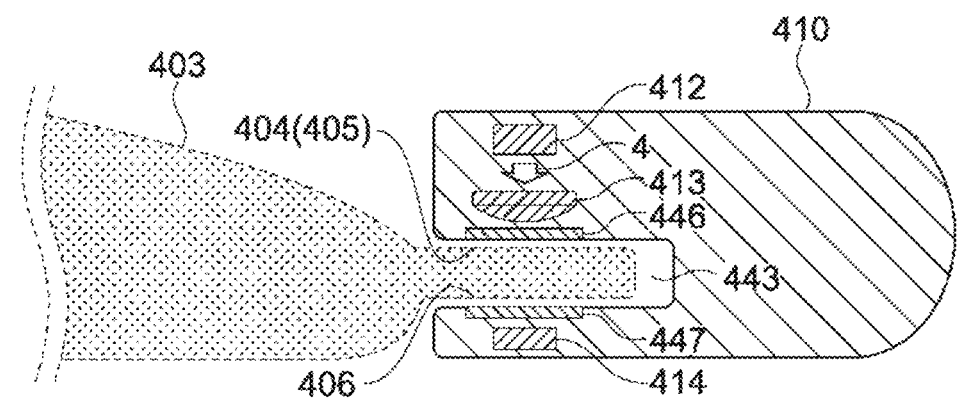

FIGS. 19A and 19B are diagrams for describing an arrangement example of the measurement apparatus. FIG. 19A is a perspective view showing an arrangement of a measurement apparatus 410 and a pack 403 for culturing. FIG. 19B is a cross-sectional view taken along the line B-B of FIG. 19A. The measurement apparatus 410 has a configuration of approximately similar to that of the measurement apparatus 210 shown in FIG. 6, for example. Illustration of the power feeder/image receiver and the like is omitted from FIGS. 19A and 19B. As a matter of course, the measurement apparatus 410 having a configuration approximately similar to that of the measurement apparatus 310 shown in FIG. 7 may be used.

The pack 403 includes observation windows 404 for observing the culture solution 1 including the cells 2. As shown in FIG. 19B, the observation windows 404 include an incident window 405 and an emission window 406 arranged with a predetermined interval therebetween such that the incident window 405 and the emission window 406 are approximately parallel to each other. The incident window 405 and the emission window 406 are constituted by a material such as transparent vinyl, acryl, and the like, for example. Moreover, the incident window 405 and the emission window 406 are arranged with an interval such that the incident window 405 and the emission window 406 can be inserted into a cavity 443 of the measurement apparatus 410.

The measurement apparatus 410 is put outside the pack 403 such that the observation windows 404 (the incident window 405 and the emission window 406) provided in the pack 403 is sandwiched by the cavity 443. In the measurement apparatus 410, illumination light 4 emitted from a light source 412 passes through the collimator lens 413 and a first optical window 446 and enters the pack 403 through the incident window 405. The illumination light 4 entering the pack 403 passes through the culture solution 1 including the cells 2 and is emitted from the emission window 406. The emitted illumination light 4 enters an image sensor 414 via a second optical window 447.

Accordingly, the measurement apparatus 410 is capable of detecting interference fringes of the illumination light 4, which are caused by the cells 2 floating inside the pack 403, in a state in which the measurement apparatus 410 is put outside the pack 403. Accordingly, states of the cells 2 and the like to be cultured in the pack 403 can be easily sensed outside the pack 403.

It should be noted that the present technology is not limited to the case where the pack 403 for culturing in which the observation windows 404 are provided is used. For example, an arbitrary culture vessel or the like in which an observation window is provided may be used. Moreover, the observation window may be provided in a flow channel or the like filled with the culture solution including the cells. Additionally or alternatively, an arbitrary configuration including the observation window may be used.

Hereinabove, the width t of the cavity of the measurement apparatus is set such that the total sum of the cross-sectional areas of the cells included in the detection space is smaller than the detection surface. A method of setting the width t of the cavity is not limited. The width t of the cavity may be set such that an area of a region in which the cells are packed in a case where the cells included in the detection space are two-dimensionally close-packed is smaller than the detection surface.

Figure 20A:
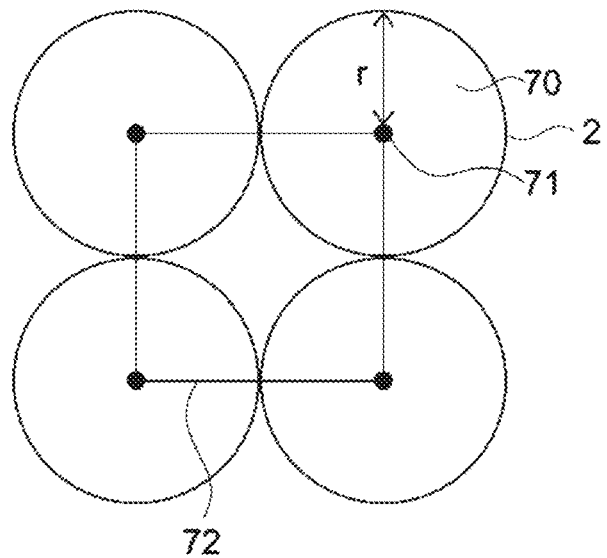
FIGS. 20A and 20B A schematic view showing examples of two-dimensional close packing of cell cross-sections.
Figure 20B:
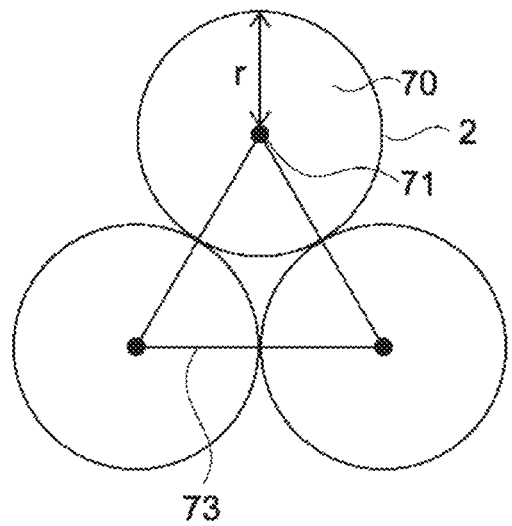

FIGS. 20A and 20B are schematic views showing an example of the two-dimensional close packing of the cell cross-sections. In FIGS. 20A and 20B, circles are used as cross-sections (cell cross-sections 70) of the cells 2. FIG. 20A is an example of close packing in which centers 71 of adjacent cells 2 are arranged in a square lattice form. FIG. 20B is an example of close packing in which centers 71 of adjacent cells 2 are arranged in a triangle lattice form.

As shown in FIG. 20A, in a case where the centers 71 of the cells 2 are arranged in a square lattice form, the occupation percentage of the cell cross-sections 70 in a square lattice 72 is a packing ratio in a two-dimensional plane. Assuming that the radius of the cell cross-section 70 is denoted by r, the area of the square lattice 72 is 4r2. Moreover, the total sum of the cell cross-sections 70 within the square lattice 72 is πr2. Therefore, the packing ratio is calculated as πr2/4r2≈0.785.

Therefore, in a case where the cells 2 are packed in a square lattice form, the total sum of the cell cross-sections 70 is an area of about 78.5% of an area of a region in which the cells are packed. In FIG. 20A, the width t of the cavity is set such that the total sum of the cross-sectional areas (cell cross-sections 70) of the cells 2 included in the detection space is smaller than 78.5% of the detection surface. That is, the width t of the cavity is set such that a total number of cells included in the detection space is smaller than a total number of cells in a case where the cells 2 are packed in a square lattice form on the detection surface.

Moreover, as shown in FIG. 20B, in a case where the centers 71 of the cells 2 are arranged in a triangle lattice form, the occupation percentage of the cell cross-section 70 in the triangle lattice 73 is a packing ratio in a two-dimensional plane. Assuming that the radius of the cell cross-section 70 is denoted by r, the area of the triangle lattice 73 is $3^{1/2}r^2$. Moreover, total sum of the cell cross-sections 70 in the triangle lattice 73 is $\pi r^2/2$. Therefore, the packing ratio is calculated as $(\pi r^2/2)/3^{1/2}r^2 \approx 0.906$.

FIG. 20B, the width t of the cavity is set such that total sum of the cross-sectional areas (the cell cross-sections 70) of the cells 2 included in the detection space is smaller than 90.6% of the detection surface. That is, the width t of the cavity is set such that a total number of cells included in the detection space is a total number of cells in a case where the cells 2 are packed in a triangle lattice form on the detection surface.

By setting the width t of the cavity in this manner by using a case where the cells 2 are two-dimensionally packed as a reference, the coherence of the illumination light 4 which passes through the cavity can be sufficiently highly maintained. Accordingly, for example, the illumination light diffracted by each cell in the liquid can be precisely detected. As a result, states of cells and the like can be sensed with sufficiently high precision.

In the above-mentioned embodiment, partially-coherent light is used as the illumination light 4 emitted from the light source 12. The present technology is not limited thereto. Approximately coherent light may be used as the illumination light.

For example, a solid-state light source such as a laser diode (LD) capable of emitting laser light having a predetermined wavelength as a light source may be used. In this case, laser light which is approximately coherent light is emitted as the illumination light from the light source. In general, the wavelength range of laser light is narrow and high coherence can be exerted. Accordingly, states of cells and the like can be sensed with high precision. Moreover, since the wavelength range is sharpened, it is unnecessary to configure the first optical window and the like as the optical filter, for example, and the cost of the apparatus can be reduced.

In the above-mentioned embodiment, the light source 12 is configured to be capable of switching and emitting light beams having wavelengths different from each other. For example, the light source may be configured to be capable of emitting light having a single wavelength. In this case, the cell information (the number of cells, the concentration, the size, the shape, and the like) can be calculated by using the illumination light having a single wavelength emitted from the light source. Accordingly, the cell state can be easily monitored in real time.

Moreover, a processing apparatus may control the display of the monitoring image on the basis of information regarding the culture solution and the like acquired using other apparatuses and the like. For example, the processing apparatus may additionally acquire information regarding the color of the culture solution, the pH value, the temperature, and the like and display a temporal change in the acquired information as the monitoring image. Also in such a case, the states and the like of the cell and the culture solution can be easily monitored and advanced production control can be achieved.

Hereinabove, the processing apparatus executes an information processing method according to the present technology including calculation of the cell information regarding the cell, control of the display of the monitoring image indicating a temporal change in the cell information, and the like. The present technology is not limited thereto. The information processing method according to the present technology may be executed by the cloud server. That is, the function of the information processing apparatus may be installed in a cloud server. In this case, the cloud server operates as the information processing apparatus according to the present technology.

Moreover, the present technology is not limited to the case where the information processing method according to the present technology is executed by a computer that acquires image data in which interference fringes of illumination light passing through liquid including a cell are recorded. The measurement system according to the present technology may be constructed by operation of the computer that acquires image data in which interference fringes of illumination light passing through liquid including a cell are recorded and another computer capable of communication via a network and the like.

That is, the information processing method and the program according to the present technology can be executed only in a computer system constituted by a single computer but also in a computer system in which a plurality of computers operate together. It should be noted that in the present disclosure, the system means collection of a plurality of components (apparatuses, modules (parts), and the like). It does not matter whether or not all the components are housed in the same casing. Therefore, a plurality of apparatuses housed in separate casings and connected to one another via a network and a single apparatus having a plurality of modules housed in a single casing are both systems.

The execution of the information processing method and the program according to the present technology by the computer system includes, for example, both of a case where calculation processing of the cell information regarding the cell, control processing of the display of the monitoring image indicating a temporal change in the cell information, and the like are executed by a single computer and a case where the respective types of processing are executed by different computers. Moreover, the execution of each of the types of processing by a predetermined computer includes causing other computers to execute some or all of those types of processing and acquiring results thereof.

That is, the information processing method and the program according to the present technology are also applicable to a configuration of cloud computing in which a plurality of apparatuses share and process a single function together via a network.

Moreover, the measurement apparatus may have all or some of the functions of the processing apparatus. That is, a function that performs calculation and the like of the cell information regarding the cell on the measurement apparatus may be installed as appropriate. Moreover, for example, the measurement apparatus and the processing apparatus may be integrally configured. As a matter of course, the display apparatus may be configured integrally with the measurement apparatus and the processing apparatus.

At least two features of the above-mentioned features according to the present technology can also be combined. That is, various types of features described in each embodiment may be arbitrarily combined without distinguishing the respective embodiments from each other. Moreover, the above-mentioned various effects are merely exemplary and are not limitative. Furthermore, other effects may be exerted.

It should be noted that the present technology can also take configurations as follows.

(1) A measurement apparatus, including:

a light source that emits illumination light;

a filling portion including a first surface portion and a second surface portion which are provided on an optical path of the illumination light and are opposite to each other, the filling portion enabling a cavity between the first and second surface portions to be filled with liquid including a cell; and a detector that detects an interference fringe of the illumination light passing through the cavity, the interference fringe being caused by the liquid including the cell.

(2) The measurement apparatus according to (1), in which the filling portion has a width from the first surface portion to the second surface portion of the cavity which is set in a manner that depends on a parameters regarding the cell.

(3) The measurement apparatus according to (2), in which the parameter regarding the cell includes at least one of a size of the cell or a concentration of the cell in the liquid.

(4) The measurement apparatus according to any one of (1) to (3), in which the detector has a detection surface approximately perpendicular to an optical path of the illumination light, and the filling portion has a detection space depending on the detection surface.

(5) The measurement apparatus according to (4), in which the width of the cavity is set such that total sum of cross-sectional areas of the cells included in the detection space is smaller than the detection surface.

(6) The measurement apparatus according to (4), in which the width of the cavity is set such that an area of a region in which cells each being the cell are packed in a case where the cells included in the detection space are two-dimensionally close-packed is smaller than the detection surface.

(7) The measurement apparatus according to any one of (2) to (6), in which the width of the cavity is smaller than 11.8 mm.

(8) The measurement apparatus according to any one of (1) to (7), in which the illumination light is approximately coherent light or partially-coherent light.

(9) The measurement apparatus according to any one of (1) to (8), in which the first surface portion includes a first optical window that the illumination light emitted from the light source enters, and the second surface portion includes a second optical window which is arranged approximately parallel to the first optical window and emits the illumination light passing through the filling portion.

(10) The measurement apparatus according to (9), in which the first optical window is an optical filter that permits some wavelength components of the illumination light to pass therethrough.

(11) The measurement apparatus according to any one of (1) to (10), further including a collimator which is arranged between the light source and the filling portion and collimates the illumination light.

(12) The measurement apparatus according to any one of (1) to (11), in which the detector generates image data in which an interference fringe of the illumination light is recorded.

(13) The measurement apparatus according to (12), in which the light source is capable of switching and emitting light beams having wavelengths different from each other as the illumination light, and the detector generates a plurality of pieces of image data respectively corresponding to the light beams having wavelengths different from each other.

(14) The measurement apparatus according to (13), further including a color-information calculation unit that calculates color information of the liquid including the cell on the basis of the plurality of pieces of image data.

(15) The measurement apparatus according to any one of (1) to (14), in which the cell includes an immune cell.

(16) The measurement apparatus according to any one of (1) to (15), in which the liquid including the cell includes a liquid culture medium to which a pH indicator is added.

(17) The measurement apparatus according to any one of (11) to (16), which is put in the liquid including the cell.

(18) An information processing apparatus, including:

an acquisition unit that acquires image data in which an interference fringe of illumination light passing through liquid including a cell is recorded;

a calculation unit that calculates cell information regarding the cell by performing propagation calculation on the illumination light on the basis of the image data; and a display controller that controls display of a monitoring image indicating a temporal change in the cell information.

(19) The information processing apparatus according to (18), in which the calculation unit calculates at least one of the number of cells, a concentration, a size, or a shape of the cell as the cell information.

(20) The information processing apparatus according to (18) or (19), in which the monitoring image includes a graph indicating a temporal change in the cell information.

(21) The information processing apparatus according to any one of (18) to (20), in which the calculation unit calculates liquid information regarding the liquid including the cell on the basis of the image data, and the monitoring image indicates a temporal change in the liquid information.

(22) The information processing apparatus according to (21), in which the acquisition unit acquires a plurality of pieces of image data respectively corresponding to a plurality of light beams emitted as the illumination light, the plurality of light beams being different from each other in wavelength, and the calculation unit calculates color information of the liquid including the cell as the liquid information on the basis of the plurality of pieces of image data.

(23) The information processing apparatus according to (22), in which the monitoring image includes a map indicating a temporal change in the color information.

(24) The information processing apparatus according to (22) or (23), in which the calculation unit calculates display color information for displaying a color of the liquid including the cell as the color information, and the monitoring image includes a map indicating a temporal change in the display color information.

(25) The information processing apparatus according to (23) or (24), in which the display controller displays each of a graph indicating a temporal change in the cell information and a map indicating a temporal change in the liquid information in an overlapping manner.

(26) The information processing apparatus according to any one of (22) to (25), in which the calculation unit calculates a pH value of the liquid including the cell on the basis of the color information, and the monitoring image includes a graph indicating a temporal change in the pH value.

(27) The information processing apparatus according to any one of (21) to (26), in which the monitoring image includes a numerical value indicating at least one of the cell information or the liquid information.

(28) The information processing apparatus according to any one of (18) to (27), in which the display controller displays, in the monitoring image, a range within which a temporal change in the cell information is normal.

(29) The information processing apparatus according to any one of (18) to (28), in which the calculation unit calculates a plurality of pieces of intermediate image data respectively corresponding to a plurality of intermediate planes through which the illumination light passes in the liquid including the cell by performing propagation calculation on the illumination light.

(30) The information processing apparatus according to (29), in which the calculation unit calculates a position of the cell in a plane direction perpendicular to an optical-path direction of the illumination light on the basis of the plurality of pieces of intermediate image data.

(31) The information processing apparatus according to (30), in which the calculation unit calculates the number of cells on the basis of the position of the cell.

(32) The information processing apparatus according to any one of (29) to (31), in which the calculation unit calculates luminance information with respect to each of the plurality of pieces of intermediate image data, and calculates a position of the cell in the optical-path direction on the basis of a change in the luminance information in the optical-path direction.

(33) The information processing apparatus according to (32), in which
the calculation unit calculates at least one of a size or a shape of the cell whose position in the optical-path direction is calculated.

(34) The measurement apparatus according to any one of (18) to (33), in which
the cell includes an immune cell.

(35) The measurement apparatus according to any one of (18) to (34), in which
the liquid including the cell includes a liquid culture medium to which a pH indicator is added.

(36) An information processing method, including:
by a computer system,
acquiring image data in which an interference fringe of illumination light passing through liquid including a cell is recorded;
calculating cell information regarding the cell by performing propagation calculation on the illumination light on the basis of the image data; and
controlling display of a monitoring image indicating a temporal change in the cell information.

(37) A program that causes a computer system to execute:
a step of acquiring image data in which an interference fringe of illumination light passing through liquid including a cell is recorded;
a step of calculating cell information regarding the cell by performing propagation calculation on the illumination light on the basis of the image data; and
a step of controlling display of a monitoring image indicating a temporal change in the cell information.

REFERENCE SIGNS LIST

O optical axis
1 culture solution
2, C1 to C8 cell
3, 403 pack
4 illumination light
10, 210, 310, 410 measurement apparatus
11 casing
12, 412 light source
13, 413 collimator lens
14, 414 image sensor
16 detection surface
17 focal plane
20 processing apparatus
21 acquisition unit
22 calculation unit
23 display controller
43, 443 cavity
44 first surface
45 second surface
46, 446 first optical window
47, 447 second optical window
48 detection space
50 monitoring image
56 color map
57a to 57c graph
58 normal range
60 image constituted by image data
61 image constituted by focal image data
70 cell cross-section
100 measurement system

The invention claimed is:

1. A measurement apparatus, comprising:
a light source configured to emit illumination light;
a filling portion including:
a first surface portion and a second surface portion which are provided on an optical path of the illumination light and are opposite to each other, the filling portion enabling a cavity between the first surface portion and the second surface portion to be filled with liquid including one or more cells, wherein the filling portion has:
a width from the first surface portion to the second surface portion of the cavity which is set in a manner that depends on a size of a cell of the one or more cells, and
a detection space, which is an inner space of the cavity through which the illumination light passes; and
a detector including a detection surface that is approximately perpendicular to the optical path of the illumination light, wherein the width of the cavity is set such that a total sum of cross-sectional areas of the one or more cells included in the detection space is smaller than an area of the detection surface, and wherein the detector is configured to detect an interference fringe of the illumination light that passes through the cavity, the interference fringe being caused by the liquid including the one or more cells.

2. The measurement apparatus according to claim 1, wherein
the manner in which the width of the filling portion is set further depends on a concentration of the one or more cells in the liquid.

3. The measurement apparatus according to claim 1, wherein
a bottom surface of the detection space has a same shape as the detection surface.

4. The measurement apparatus according to claim 1, wherein
the width of the cavity is set such that an area of a region in which the one or more cells are packed, in a case where the one or more cells included in the detection space are two-dimensionally close-packed, is smaller than the area of the detection surface.

5. The measurement apparatus according to claim 1, wherein
the illumination light is approximately coherent light or partially-coherent light.

6. The measurement apparatus according to claim 1, wherein
the first surface portion includes a first optical window that the illumination light emitted from the light source enters, and
the second surface portion includes a second optical window which is arranged approximately parallel to the first optical window and emits the illumination light passing through the filling portion.

7. The measurement apparatus according to claim 6, wherein
the first optical window is an optical filter that is configured to permit some wavelength components of the illumination light to pass therethrough.

8. The measurement apparatus according to claim 1, further comprising
a collimator which is arranged between the light source and the filling portion and is configured to collimate the illumination light.

9. The measurement apparatus according to claim 1, wherein
the detector is further configured to generate image data in which the interference fringe of the illumination light is recorded.

10. The measurement apparatus according to claim 9, wherein
the light source is further configured to switch between light beams having wavelengths different from each other to emit the illumination light, and
the detector is further configured to generate a plurality of pieces of the image data respectively corresponding to the light beams having the wavelengths different from each other.

11. The measurement apparatus according to claim 10, further comprising:
a color-information calculation unit that is configured to calculate color information of the liquid including the one or more cells on a basis of the plurality of pieces of the image data.

12. The measurement apparatus according to claim 11, wherein
the color-information calculation unit calculates a pH value of a liquid culture medium included in the liquid, based on the plurality of pieces of the image data.

13. The measurement apparatus according to claim 1, wherein the measurement apparatus is immerged in the liquid including the one or more cells such that the cavity gets filled with the liquid.

14. The measurement apparatus according to claim 1, wherein
the manner in which the width of the filling portion is set further depends on coherence of the illumination light.

15. The measurement apparatus according to claim 1, wherein
the detection space is a columnar space such that the width of the cavity is a height of the detection space.

16. The measurement apparatus according to claim 11, wherein
the color-information calculation unit is further configured to calculate a mean luminance value for each of the plurality of pieces of the image data corresponding to the light beams having the wavelengths different from each other, and
the calculation of the color information of the liquid is based on the mean luminance value for each of the plurality of pieces of the image data.

17. A measurement apparatus, comprising:
a casing that includes a base portion, a first protrusion portion, and a second protrusion portion, wherein the first protrusion portion and the second protrusion portion protrude from the base portion in a same direction and are spaced apart by a predetermined distance, and wherein:
a cavity is formed between the first protrusion portion and the second protrusion portion, and has a width equivalent to the predetermined distance,
the cavity is enabled to be filled with liquid that includes one or more cells, and
the predetermined distance is set based on a size of a cell of the one or more cells;
a light source arranged in the first protrusion portion and configured to emit illumination light; and
a detector arranged inside the second protrusion portion and configured to detect an interference fringe of the illumination light that passes through the cavity, the interference fringe being caused by the liquid including the one or more cells.

18. A measurement apparatus, comprising:
a light source configured to emit illumination light;
a filling portion including:
a first surface portion and a second surface portion which are provided on an optical path of the illumination light and are opposite to each other, the filling portion enabling a cavity between the first surface portion and the second surface portion to be filled with liquid including one or more cells, wherein the filling portion has:
a width from the first surface portion to the second surface portion of the cavity which is set in a manner that depends on a size of a cell of the one or more cells, and
a detection space, which is an inner space of the cavity through which the illumination light passes; and
a detector including a detection surface that has a same shape as a bottom surface of the detection space and that is approximately perpendicular to the optical path of the illumination light, wherein the detector is configured to detect an interference fringe of the illumination light that passes through the cavity, the interference fringe being caused by the liquid including the one or more cells.

* * * * *